(12) United States Patent
Schelling

(10) Patent No.: US 9,011,507 B2
(45) Date of Patent: Apr. 21, 2015

(54) COMPRESSION PLATE KIT AND METHODS FOR REPAIRING BONE DISCONTINUITIES

(75) Inventor: Craig Schelling, Liberty, UT (US)

(73) Assignee: Orthopro LLC, Salt Lake City, UT (US)

( * ) Notice: Subject to any disclaimer, the term of this patent is extended or adjusted under 35 U.S.C. 154(b) by 875 days.

(21) Appl. No.: 13/075,871

(22) Filed: Mar. 30, 2011

(65) Prior Publication Data

US 2011/0224734 A1 Sep. 15, 2011

Related U.S. Application Data

(63) Continuation-in-part of application No. 12/607,870, filed on Oct. 28, 2009, now Pat. No. 8,162,996.

(51) Int. Cl.

| | | |
|---|---|---|
| *A61B 17/04* | (2006.01) | |
| *A61B 17/84* | (2006.01) | |
| *A61F 2/08* | (2006.01) | |
| *A61B 17/80* | (2006.01) | |
| *A61B 17/70* | (2006.01) | |
| *A61B 17/86* | (2006.01) | |
| *A61B 17/88* | (2006.01) | |
| *A61B 17/00* | (2006.01) | |

(52) U.S. Cl.
CPC ......... *A61B 17/8061* (2013.01); *A61B 17/7079* (2013.01); *A61B 17/8014* (2013.01); *A61B 17/861* (2013.01); *A61B 17/8866* (2013.01); *A61B 17/863* (2013.01); *A61B 2017/00004* (2013.01)

(58) Field of Classification Search
CPC .................................................... A61B 17/688
USPC ................................................. 606/324, 105
See application file for complete search history.

(56) References Cited

U.S. PATENT DOCUMENTS

| | | | |
|---|---|---|---|
| 3,528,085 A | 9/1970 | Reynolds | |
| 4,408,601 A | 10/1983 | Wenk | |

(Continued)

FOREIGN PATENT DOCUMENTS

DE 4127303 2/1893

OTHER PUBLICATIONS

U.S. Appl. No. 12/607,870, Sep. 19, 2011, Office Action from U.S. Appl. No. 12/607,870.

(Continued)

*Primary Examiner* — Kevin T Truong
*Assistant Examiner* — Christine Nelson
(74) *Attorney, Agent, or Firm* — Duane Morris LLP

(57) ABSTRACT

A compression plate kit that allows for manual compression of a bone discontinuity includes a bone plate, two or more reduction fasteners in the form of screws or pins, for example, and a compression clamp. The compression clamp can include engagement members configured to engage the reduction screws or pins, thereby allowing a practitioner to compress a bone discontinuity by manually closing the compression clamp. One or more implementations of a kit of the present invention can provide a practitioner with physical or tactile feedback during the compression of a bone discontinuity, and thus, provide the practitioner with the ability to better control the compression and spacing of bone portions during a reduction. One implementation of the kit includes a coupler for coupling the upper portions of the reduction fasteners together for selective fine tuning adjustments.

15 Claims, 15 Drawing Sheets

(56) References Cited

U.S. PATENT DOCUMENTS

| | | | |
|---|---|---|---|
| 5,746,741 | A | 5/1998 | Kraus |
| 5,968,046 | A | 10/1999 | Castleman |
| 6,520,964 | B2 | 2/2003 | Tallarida et al. |
| 6,610,067 | B2 | 8/2003 | Tallarida et al. |
| 6,679,917 | B2 | 1/2004 | Ek |
| 6,692,503 | B2 | 2/2004 | Foley et al. |
| 6,746,449 | B2 | 6/2004 | Jones et al. |
| 6,916,320 | B2 | 7/2005 | Michelson |
| 7,090,674 | B2 | 8/2006 | Doubler et al. |
| 7,090,676 | B2 | 8/2006 | Huebner et al. |
| 7,537,596 | B2 | 5/2009 | Jensen |
| 7,537,604 | B2 | 5/2009 | Huebner |
| 7,914,536 | B2 | 3/2011 | MacDonald et al. |
| 8,162,996 | B2 | 4/2012 | Schelling |
| 2002/0120273 | A1 | 8/2002 | Needham et al. |
| 2002/0188297 | A1 | 12/2002 | Dakin et al. |
| 2005/0277941 | A1 | 12/2005 | Trumble et al. |
| 2006/0217735 | A1 | 9/2006 | MacDonald |
| 2007/0270850 | A1 | 11/2007 | Geissler |
| 2009/0210010 | A1 | 8/2009 | Strnad et al. |
| 2009/0210011 | A1 | 8/2009 | Den Hartog et al. |
| 2009/0210013 | A1 | 8/2009 | Kay et al. |
| 2011/0098757 | A1 | 4/2011 | Schelling |

OTHER PUBLICATIONS

U.S. Appl. No. 12/607,870, Feb. 27, 2012, Notice of Allowance.
U.S. Appl. No. 12/607,870, Apr. 4, 2012, Issue Notification.
Pages from website www.arthrosurface.com, (including www.arthrosurface.com/checkmate), printed on Jan. 10, 2013 (6 pages).
Arthrosurface, "When it's your last move," Podiatry Today, Dec. 2012 (2 pages).
Arthrosurface, "When it's your last move," Checkmate MTP Arthrodesis System, Technique Guide (7 pages), Copyright 2012.
Arthrosurface, "When it's your last move," Checkmate MTP Arthrodesis System brochure (2 pages), Copyright 2012.
Brochure entitled "2.4 mm/2.7 mm Variable Angle LCP Forefoot/Midfoot System—Procedure-specific," copyright 2010 (95 pages).
Brochure entitled "Aesculap Spine—Socon," available upon information and belief at least as early as 2007 (20 pages).
Brochure entitled "Aesculap Spine—Casper Cervical Retractor System," copyright 2009 (16 pages).
Article entitled "S$^4$FRI (Fraction Reduction Instrument) Aesculap Implant Systems, LLC Stresses the Importance of Precision and Control in Fracture Reduction of the Spine," copyright 2011, printed May 24, 2011 (4 pages).
Illustrations of Aesculap Socon Spinal Fixation System, which were available, upon information and belief, at least as early as Mar. 2010 (2 images, 1 page).
U.S. Appl. No. 13/075,871 entitled Compression Plate Kit and Methods for Repairing Bone Discontinuities, filed Mar. 30, 2011, including filing receipt, specification and drawings (76 pages).
International Search Report and Written Opinion from PCT/US2010/053681 dated Dec. 21, 2010, 10 pages.
Spine and Spine, Global Spine Products Overview, pp. 1-212, document available at www.spineandspine.com/old/pdf/019.pdf, available, on information and belief, at least as early as May 15, 2007.
European Patent Office, English Translation of Abstract for DE4127303 (1 page).
Orthohelix, MaxLock Extreme Innovative Plate and Screw System, Copyright 2009, pp. 1-14, Medina, OH, available, on information and belief, at least as early as Sep. 22, 2009.
Wright Medical Technology, Inc., Charlotte, Copyright 2007, pp. 1-20, Arlington, TN.
Wright Medical Technology, Inc., Locon-T Surgical Technique, Copyright 2005, pp. 1-12, Arlington, TN.
Wright Medical Technology, Inc., Foot and Ankle Products, pp. 1-20, documents available under links found at http://www.wmt.com/footandankle/bytype.asp, available, on information and belief, at least as early as Sep. 22, 2009.

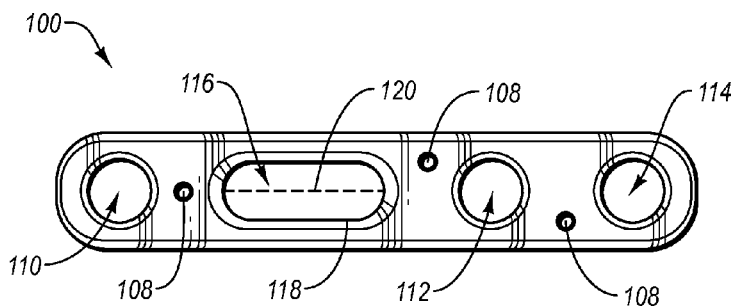
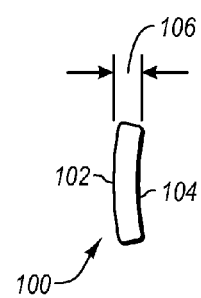
Figure 1A
Figure 1B
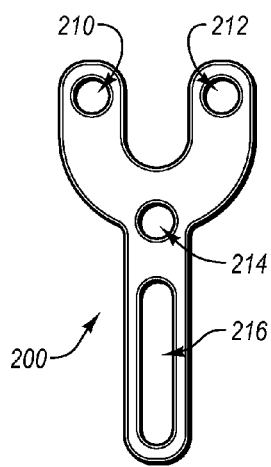
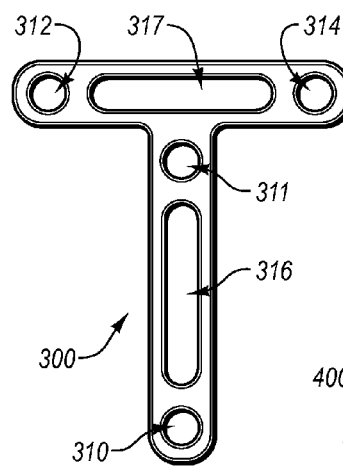
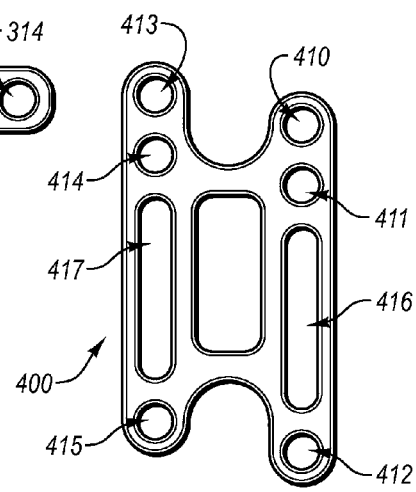
Figure 2
Figure 3
Figure 4

COMPRESSION PLATE KIT AND METHODS FOR REPAIRING BONE DISCONTINUITIES

CROSS-REFERENCE TO RELATED APPLICATIONS

This application is a continuation-in-part of prior U.S. patent application Ser. No. 12/607,870 entitled COMPRESSION PLATE KIT AND METHODS FOR REPAIRING BONE DISCONTINUITIES, filed Oct. 28, 2009 to Craig Schelling, which is incorporated herein by reference in its entirety.

BACKGROUND OF THE INVENTION

1. The Field of the Invention

The present invention relates generally to a kit for repairing bones. More specifically, the invention relates to a compression plate kit configured to permit manual reduction of bone discontinuities and methods of using the compression plate kit for repairing bone discontinuities.

2. Background and Relevant Art

Bones perform a variety of important functions, including support, movement, protection, storage of minerals, and formation of blood cells. To help ensure that bones can perform these important functions, and to reduce pain or correct disfigurement, injured bones should be promptly and properly repaired. In repairing fractured or otherwise injured bones, it is common for a practitioner to use a fixation device that both reinforces the bone and keeps it properly aligned during healing. One common type of fixation device is a bone plate.

To use a bone plate to repair a discontinuity of a bone, a practitioner typically (1) selects an appropriate plate, (2) reduces the discontinuity (e.g., sets the fracture), and (3) fastens the plate to the bone. The plate is usually secured to bone portions disposed on opposing sides of the discontinuity using suitable fasteners, such as screws and/or wires, so that the bone portions are fixed in proper alignment. It is often important to reduce a bone discontinuity to help ensure proper alignment, and thereby decrease pain, prevent later deformity, and help allow the bone to heal properly and quickly.

One aspect of reducing a bone discontinuity involves compressing bone portions on opposing sides of the discontinuity together and/or otherwise adjusting the bone portions to help ensure proper spacing, or lack thereof, prior to fixation of the bone plate. Ensuring proper spacing between opposing bone portions of a discontinuity can be particularly important because in some cases any space between the two bones can result in prolonged healing and complete ossification of the gap between the bones. Such changes to the shape of the bone can alter the mechanics of the bone in a manner that could weaken or result in changes to the biomechanics of the patient's body. Additionally, such spacing can result in abnormal growth in the bone that can create additional complications. To aid in reducing bone discontinuities, some bone plates, called compression plates, not only secure bone fragments or portions together, but also impart relative movement between the bone portions to help ensure the bone portions are properly spaced and aligned.

Specifically, compression plates typically include fixation holes and a compression slot (a tapered or inclined slot that causes a screw to move from one end to the other as the screw is tightened). To use a compression plate, a practitioner attaches the compression plate to one side of the bone discontinuity using one or more fasteners. The practitioner then inserts a screw within the compression slot, as far from the discontinuity as possible, and begins tightening the screw within the compression slot. During tightening, the head of the screw engages the tapered or inclined surfaces of the compression slot causing the screw, and the bone portion(s) connected thereto, to move along the compression slot, thereby compressing bone portions on opposing sides of the discontinuity together.

Unfortunately, conventional compression plates tend to suffer from a number of drawbacks. For example, the length of conventional compression slots, and thus the amount of compression provided thereby, is limited by the size and shape of the head of the screw being used therewith. Thus, most conventional compression plates allow for a compression of 2 millimeters for less. Furthermore, controlling the exact amount of compression or spacing between bone portions using conventional compression plates can be difficult. Specifically, the amount of compression generated between two bone portions using a conventional compression plate is based on the initial positioning of the screw within the compression slot and on how tight the screw is fixed within the compression slot; neither of which provide any quantifiable feedback to the practitioner on the actual amount of compression between bone portions. Thus, a practitioner is often forced to make an educated guess on the exact compression between portions of a bone discontinuity when using conventional compression plates.

BRIEF SUMMARY OF THE INVENTION

Implementations of the present invention solve one or more of the foregoing problems in the art with systems, methods, and apparatus that provide a great deal of functional versatility in correcting bone discontinuities. For example, one or more implementations of the present invention includes a compression plate kit that allows for manual compression control of a bone discontinuity for improved repair of fractures, fusions, and other bone discontinuities. Additionally, one or more implementations of the present invention include compression plate kits that allow for the compression of larger gaps between bones. Accordingly, implementations of the present invention can allow for efficient and accurate correction of various different types of bone injury.

For example, one implementation of a surgical kit for use in correcting a discontinuity between a first bone portion and a second bone portion includes a bone plate having one or more fixation holes and at least one elongated slide channel. The kit further includes two or more reduction fasteners each having a head and a threaded shaft. A first reduction fastener is adapted to be inserted within a fixation hole of the bone plate, and a second reduction fastener is adapted to be inserted within the at least one elongated slide channel. Additionally, the kit includes a compression clamp having a pair of engagement members adapted to engage the heads of the first and second reduction fasteners. The compression clamp draws the second reduction fastener along the at least one elongated slide channel toward the first reduction fastener, thereby compressing a bone discontinuity.

Another implementation of a kit for use in correcting bone discontinuities includes a bone plate adapted to secure a first bone portion to a second bone portion. The bone plate has a first fixation hole, an elongated slide channel, and a second fixation hole. The kit further includes a first reduction fastener having a first head including a first engagement groove extending radially therein. The first reduction fastener is adapted to be inserted within the second fixation hole of the bone plate and secured to the first bone portion. The kit also includes a second reduction fastener having a second head including a second engagement groove extending radially therein. The second reduction fastener is adapted to be inserted within the elongated slide channel of the bone plate and secured to the second bone portion. Additionally, the kit includes a compression clamp having a first hook and a second hook. The first hook is sized and configured to be at least partially inserted within the first engagement groove and engage the first head of the first reduction fastener. The second hook is sized and configured to be at least partially inserted within the second engagement groove and engage the second head of the second reduction fastener. The compression clamp is thus configured to draw the second reduction fastener along the elongated slide channel of the bone plate toward the first reduction fastener, thereby pulling the second bone portion toward the first bone portion.

In addition to the foregoing, an implementation of a method of surgically repairing a bone discontinuity involves securing a first reduction fastener within a first fixation hole of a bone plate and to a first bone portion. The method also involves securing a second reduction fastener within an elongated slide channel of the bone plate and to a second bone portion. Additionally, the method involves positioning a first engagement member of a compression clamp about a head of the first reduction fastener. The method further involves positioning a second engagement member of the compression clamp about a head of the second reduction fastener. Also, the method involves closing the compression clamp, thereby drawing the second reduction fastener and the second bone portion along the elongated slide channel toward the first reduction fastener and the first bone portion. The method additionally involves securing a fixation fastener within a second fixation hole of the bone plate and to the second bone portion.

In another implementation of the present invention, the reduction fasteners employed comprise smooth elongate shafts and the engagement members configured to contact the shafts for reduction purposes have corresponding mounting portions, such as mounting chambers having apertures, the mounting chambers being slidably mounted on and engaging the smooth elongate shafts.

In yet another implementation of the present invention, a kit for correcting bone discontinuities comprises a coupler configured to be coupled to the upper portions of the reduction fasteners such that the positions of the reduction fasteners can be adjusted in fine tuned increments.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the figures are not drawn to scale, and that elements of similar structure or function are generally represented by like reference numerals for illustrative purposes throughout the figures. Understanding that these drawings depict only typical embodiments of the invention and are not therefore to be considered to be limiting of its scope, the invention will be described and explained with additional specificity and detail through the use of the accompanying drawings in which:

FIG. 1A illustrates a plan view of a bone plate in accordance with an implementation of the present invention;

FIG. 1B illustrates an end view of the bone plate of FIG. 1A;

FIG. 2 illustrates a plan view of another bone plate in accordance with an implementation of the present invention;

FIG. 3 illustrates a plan view of an additional bone plate in accordance with an implementation of the present invention;

FIG. 4 illustrates a plan view of yet another bone plate in accordance with an implementation of the present invention;

DETAILED DESCRIPTION OF THE PREFERRED EMBODIMENTS

Figure 5:
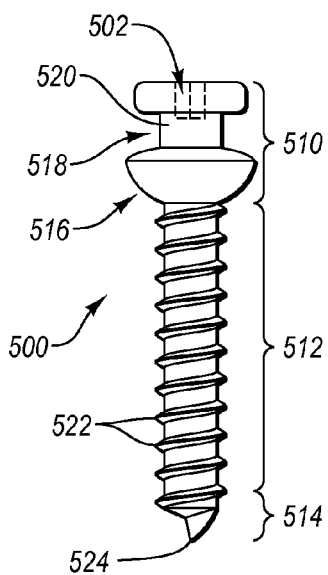
FIG. 5 illustrates a side perspective-view of a reduction fastener in accordance with an implementation of the present invention.

Implementations of the present invention provide systems, methods, and apparatus that provide a great deal of functional versatility in correcting bone discontinuities. For example, one or more implementations of the present invention includes a compression plate kit that allows for manual compression control of a bone discontinuity for improved repair of fractures, fusions, and other bone discontinuities. Additionally, one or more implementations of the present invention include compression plate kits that allow for the compression of larger gaps between bones. Accordingly, implementations of the present invention can allow for efficient and accurate correction of various different types of bone injury.

For instance, according to one implementation of the present invention, a compression plate kit allows a practitioner to not only manually control the compression and reduction of a bone discontinuity, but to also feel and/or see the amount of compression. The ability to feel and/or see the amount of compression can allow the practitioner to properly set the spacing and alignment between bone portions of a bone discontinuity, and thereby help ensure proper healing. In other words, one or more implementations of the present invention provide a practitioner with physical or tactile feedback during the compression of a bone discontinuity, and thus, provide the practitioner with the ability to better control the compression and spacing of bone portions during a reduction.

More particularly, one or more implementations of a bone plate kit of the present invention include a bone plate, one or more fasteners, and a compression clamp. The bone plate is adapted to be secured to opposing bone portions of a bone discontinuity via a pair of reduction fasteners. A first reduction fastener is adapted to be secured within an elongated slide channel of the bone plate and to a first portion of the bone discontinuity. The second reduction fastener is adapted to be secured within a fixation hole of the bone plate and to a second portion of the bone discontinuity. The compression clamp is adapted to engage the reduction fasteners. After engaging the reduction fasteners with the compression clamp, a practitioner closes the compression clamp, thereby drawing the second reduction fastener (and the second bone portion secured thereto) along the elongated slide channel toward the first reduction fastener (and the first bone portion secured thereto). Because the amount of force the practitioner applies to the compression clamp controls the amount of compression between the bone portions of the bone discontinuity, the bone plate kit provides the practitioner with physical feedback on the distance reduced and the amount of compression between the bone portions of a bone discontinuity.

As previously mentioned, one or more implementations of the present invention are directed towards a compression plate kit and methods of using such a kit to repair bone fractures, fusions, and other bone discontinuities. The various elements of a kit in accordance with one or more implementations will be described with reference to FIGS. 1A-8; after which an exemplary surgical method of repairing a bone discontinuity using a compression plate kit of the present invention will be described with references to FIGS. 9-10F.

FIGS. 1A and 1B, and the corresponding text, illustrate or describe an exemplary bone plate 100 of a compression plate kit according to one or more implementations of the present invention. As an initial matter, bone plates in accordance with one or more implementations of the present invention generally comprise a relatively low-profile (or plate-like) fixation device configured to stabilize a bone discontinuity by attachment to bone portions on opposing sides thereof. For example, the bone plate 100 is configured to span a bone discontinuity (such as, for example, a fracture, a cut, or a bone joint) so that the bone plate 100 fixes the relative positions of bone portions disposed on opposing sides of the bone discontinuity. The bone plate 100 is generally configured to contact an outer surface of the bone, and thus, may be positioned at least substantially exterior to the bone. The bone plate 100 may be left in place permanently or removed after the associated bone discontinuity has partially or completely healed.

The bone plate 100 has a structurally sturdy yet configurable construction. For example, the bone plate 100 is stiff and strong enough to provide support to opposing portions of a bone discontinuity, yet flexible (e.g., resilient) enough to avoid significantly straining the bone. The bone plate 100 may comprise biocompatible materials such as, for example, titanium or titanium alloys, cobalt chromium, stainless steel, polymers, or ceramics, and/or bioabsorbable materials. In any case, the bone plate 100 is configured to reduce irritation to the bone and surrounding tissue. For example, as previously mentioned, the bone plate 100 has a low profile to reduce protrusion into adjacent tissues.

As shown in FIG. 1B, the bone plate 100 includes a distal (bone-opposing) surface 102 and a proximal (bone-facing) surface 104. One or both of the distal 102 and proximal 104 surfaces can optionally be contoured or otherwise configured to correspond with a surface of a target bone (or bones), so that the bone plate 100 maintains a low profile and fits onto the bone(s). For example, the proximal surface 104 of the bone plate 100 may be generally complementary in contour to the surface of a bone.

The thickness 106 of the bone plate 100 is defined by the distance between the proximal 104 and distal 102 surfaces of the bone plate 100. In some implementations of the present invention, the thickness 106 of the bone plate 100 varies along the length of the bone plate 100. For example, portions of the bone plate 100 configured to extend over a tuberosity or the like may have a smaller thickness, thereby reducing profile and/or rigidity. Additionally, the thickness 106 of the bone plate 100 may differ depending upon the intended use of the bone plate 100. For example, a thinner bone plate 100, such as that shown in FIGS. 1A-1B, is configured for use on smaller bones and/or on bones or bone regions where soft tissue irritation is a greater concern.

Additionally, the thickness 106 of the bone plate 100 also may be configured to allow for further contouring and bending of the bone plate 100. For example, the thickness of the bone plate 100 shown in FIGS. 1A and 1B allows a practitioner to use bending pliers or other tools to provide the bone plate 100 with dorsal and/or other curvature, so as to conform the bone plate 100 to the features of a bone.

As explained in greater detail below, the bone plate 100 is configured to be secured to opposing bone portions of a bone discontinuity and to aid in compressing the bone portions together. To facilitate attachment to, and compression of, two or more bone portions, the bone plate 100 includes a plurality of through-holes or openings. The through-holes or openings are adapted to receive fasteners for securing the bone plate 100 to various bone portions of a bone discontinuity. Additionally, the through-holes or openings work cooperatively with fasteners and a compression clamp to allow compression of a bone discontinuity, as explained in greater detail below. Alternatively, or additionally, the through-holes or openings are adapted to alter the local rigidity of the bone plate 100, to permit the bone plate 100 to be manipulated with a tool (such as bending pliers), and/or to facilitate blood flow to a fracture or surgical site to promote healing.

The plurality of through-holes or openings can include one or more attachment holes. For example, FIG. 1A shows that the bone plate 100 includes three attachment holes 108. As shown by FIG. 1A, the attachment holes 108 are sized and configured to receive a K-wire or other similar guide wire. As explained in greater detail below, the attachment holes 108 are adapted to be used to temporarily secure the bone plate 100 to one or more bone portions in preparation of the placement of additional and/or more permanent fasteners.

In addition to attachment holes 108, the plurality of through-holes or openings can also include one or more fixation holes configured to receive one or more fixation fasteners that fix the bone plate to a bone, as explained in greater detail below. For example, FIG. 1A illustrates the bone plate 100 includes three fixation holes 110, 112, 114. One will appreciate in light of the disclosure herein that the fixation holes of the bone plates of the present invention may have any suitable position within the bone plate. For example, as shown in FIG. 1A, the fixation holes 110, 112, 114 are positioned in a line along the center portion of the bone plate 100. In alternative implementations, the fixation holes of the bone plate are arranged nonlinearly in a curved or staggered arrangement.

Additionally, in one or more implementations, the fixation holes 110, 112, 114 comprise threaded openings. In some implementations, the threads of the fixation holes 110, 112, 114 are configured to direct fixation fasteners inserted therein along non-parallel paths relative to the openings to help ensure that the fixation fasteners have adequate contact with the bone. Additionally or alternatively, the threads of the fixation holes 110, 112, 114 are configured to lock a fixation fastener inserted therein to the bone plate 100 and a portion of bone.

The bone plates of the present invention include one or more slide channels, e.g., an elongated slide channel. An elongated slide channel is any elongate opening having a length that is greater than its width. In some implementations, the length of the elongated slide channel is at least approximately twice the width of the elongated slide channel. In yet further implementations, the length of the elongated slide channel may be between approximately 2 and 20 times the width of the elongated slide channel. For example, FIG. 1A illustrates that the bone plate 100 has an elongated slide channel 116 with a length approximately 2.5 times the width thereof. As explained in greater detail below, the length of the elongated slide channel 116 determines the amount of compression provided by the bone plate 100. Thus, in one or more implementations the length of the elongated slide channel 116 is tailored based on the bone discontinuity with which the bone plate 100 is intended to be used.

As illustrated in implementation of FIG. 1A, the elongated slide channel 116 includes a counterbore 118 configured to receive, at least partially, a head of a fastener. In contrast to conventional compressions slots, in one or more implementation of the present invention the counterbore 118 is substantially uniform along its length. In other words, in one or more implementations, the counterbore 118 does not include a taper or incline that causes a screw head to move along the length of the elongated slide channel 116 as the screw is tightened.

The elongated slide channels of the present invention may have any suitable location along a bone plate. For example, as shown in the implementation of FIG. 1A, the elongated slide channel 116 is disposed near the center of the bone plate 100. Additionally, the elongated slide channels may be disposed between a pair of fixation holes. For example, FIG. 1A illustrates that the elongated slide channel 116 is disposed between a first fixation hole 110 and a second fixation hole 112. Alternatively, the elongated slide channel 116 may be disposed near an end of the bone plate (as defined by the length of the bone plate 100). For example, FIG. 2 illustrates a bone plate 200, including an elongated slide channel 216 located near an end of the bone plate 200.

One will appreciate as explained in greater detail below, that the elongated slide channel 116 and the fixation holes 110, 112, 114 work cooperatively to compress a bone discontinuity and fix the bone discontinuity in place. More specifically, a first reduction fastener is secured within a fixation hole 110, 112, 114 to a first bone portion, and a second reduction fastener is secured within the elongated slide channel 116 to a second bone portion. Using a compression clamp, the second reduction fastener and second bone portion are drawn along the elongated slide channel 116 toward the first reduction fastener and first bone portion to compress a bone discontinuity. In one or more implementations of the present invention, to aid in compressing a bone discontinuity, the elongated slide channel 116 is linearly aligned with at least one fixation hole. For example, FIG. 1A illustrates that the center of three fixation holes 110, 112, 114 are linearly aligned with the longitudinal axis 120 of the elongated slide channel 116. Alternatively, FIG. 2 illustrates that only a single fixation hole 214 is aligned with the elongated slide channel 216.

Additionally, while FIG. 1A illustrates a bone plate 100 with a single elongated slide channel 116, in alternative implementations; the bone plate includes two, three, four, or any suitable number of slide channels. For example, additional implementations of a bone plate include a pair of slide channels configured to act cooperatively with each other and/or fasteners placed therein for positioning the bone plate 100 in situ and compressing one or more bone discontinuities.

One will appreciate that the number and relative positioning of the slide channels can be based upon the type, number, and size of the bone discontinuities with which the bone plate is to be used. For example, FIG. 3 illustrates a bone plate 300 with a pair of elongated slide channels 316, 317 disposed substantially orthogonally to each other. One will appreciate that the bone plate 300 is adapted to compress two bone discontinuities. Additionally, the number and location of the fixation holes can also be varied depending upon the intended use of the bone plate. For example, FIG. 3 illustrates that the bone plate 300 includes four fixation holes 310, 311, 312, 314. First and second fixation holes 310, 311 are aligned with the first elongated slide channel 316, while third and fourth fixation holes 312, 314 are aligned with the second elongated slide channel 317.

In addition, or alternatively, to orthogonal orientation, elongated slide channels can also be positioned substantially parallel to each other or at any other orientation. For example, FIG. 4 illustrates a bone plate 400 having a first elongated slide channel 416 positioned in a substantially parallel orientation relative to a second elongated slide channel 417. Additionally, FIG. 4 illustrates that the bone plate 400 includes six fixation holes, with the first three fixation holes 410, 411, 412 being aligned with the first elongated slide channel 416, and the second three fixation holes 413, 414, 415 being aligned with the second elongated slide channel 417.

Figure 11:
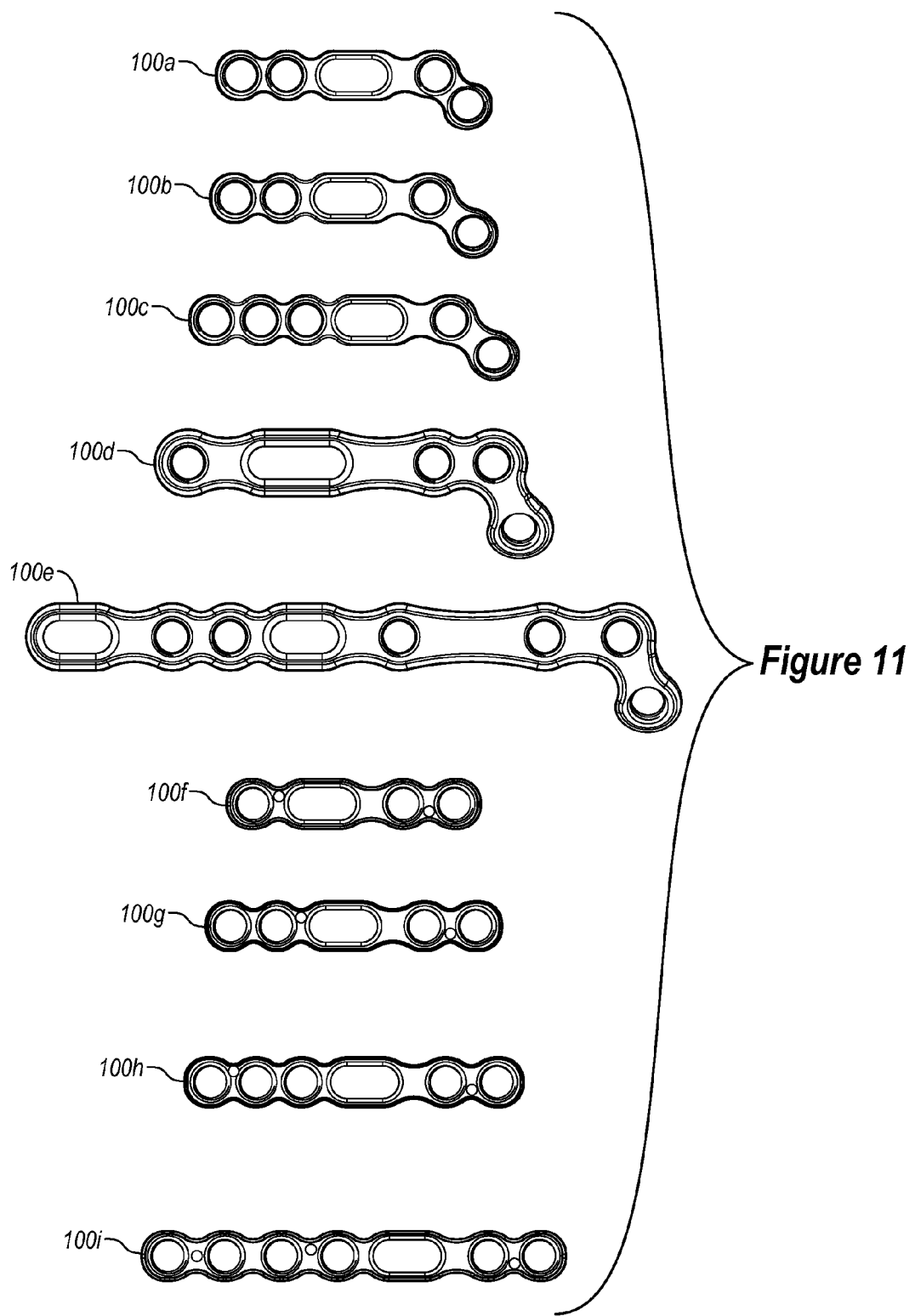
FIG. 11 illustrates additional implementations of various bone plates in accordance with implementations of the present invention.

In addition to the number and position of the elongated slide channels and the fixation holes, the bone plates of the present invention themselves can include a number of different configurations depending upon their intended use. For example, bone plates of the present invention include a linear shape (e.g., bone plate 100 of FIG. 1A), a Y-shape (e.g., bone plate 200 of FIG. 2), a T-shape (e.g., bone plate 300 of FIG. 3), a butterfly shape (e.g., bone plate 400 of FIG. 4), and other suitable shapes or configurations. Furthermore, FIG. 11 illustrates yet additional bone plates 11a-11i according to additional implementations of the present invention.

Additionally, the bone plates of one or more implementations of the present invention are configured to be used to correct bone discontinuities in or between the smaller bones of the foot or hand, such as for example, metatarsophalangeal joint fusions, lapidus procedures, or metatarsal fractures. One will appreciate, however, that the bone plates of other implementations of the present invention are configured to be used to repair any number and type of bone discontinuity. For example, the bone plates of various implementations of the present invention are configured for use on or between any suitable bones of the human body and/or other vertebrate species. Exemplary bones include bones of the arms (radius, ulna, humerus), legs (femur, tibia, fibula, patella), hands, feet, the vertebrae, scapulas, pelvic bones, cranial bones, ribs, clavicles, etc. Depending on the type of bones and type of bone discontinuities, the size and shape of the bone plate, number and position of fixation holes, and number and position of elongated slide channels vary.

As mentioned previously, in addition to a bone plate, kits of the present invention include one or more fasteners that work in conjunction with the bone plate. For example, FIG. 5 illustrates a side perspective view of an exemplary reduction fastener 500 according to an implementation of the present invention. As explained in greater detail below, the reduction fastener 500 is configured to both secure a bone plate 100, 200, 300, 400 to a portion of a bone discontinuity, and also aid in compressing bone portions of a bone discontinuity. In the illustrated implementation, the reduction fastener 500 comprises a head 510, a shaft 512, and a tip 514.

As FIG. 5 shows, the head 510 includes a recess 502 configured to receive a portion of a rotational tool, such as, for example, a drill or screw driver. More specifically, the recess comprises a void into which a portion of a rotation tool can be inserted. One will appreciate that the rotational tool may provide the force necessary to rotate the reduction fastener 500 into a portion of bone or other material. FIG. 5 illustrates that the recess 502 comprises a hexagon shape. When a rotation tool is inserted into the recess 502 and rotated, the rotational tool engages the lateral surfaces of the recess 502 in a manner so as to provide sufficient rotational torque to rotate the reduction fastener 500.

As will be appreciated by those skilled in the art, the recess 502 can comprise a variety of different types and configurations without departing from the scope and spirit of the present invention. For example, in one implementation, the recess 502 comprises a flattened slot. In yet another implementation, the recess 502 comprises a slot having a crossing pattern.

The head 510 of the reduction fastener 500 also comprises one or more engagement features that allow it (and a portion of bone secured to the reduction fastener 500) to be pulled along an elongated slide channel of a bone plate, thereby compressing a bone discontinuity. More specifically, the head 510 of the reduction fastener 500 comprises one or more engagement features configured to be engaged by a compression clamp (see FIG. 8), which a practitioner may use to draw two reduction fasteners 500 together. For example, FIG. 5 illustrates that the head 510 includes an annular engagement groove 518 extending radially therein. The annular engagement groove 518 exposes a neck 520 of reduced diameter, which is adapted to be engaged by a compression clamp.

As will be appreciated by those skilled in the art, engagement features of the head 510 are not limited to annular engagement grooves 510; thus, alternative implementations include a variety of types and configurations of engagement features. For example, in an alternative implementation, the head 510 of the reduction fastener 500 can include an engagement slot (not shown). The engagement slot comprises a hole extending through the head 510 of the reduction fastener 500, which is adapted to receive a portion of a compression clamp. In yet a further implementation of the present invention, the recess 502 of the head 510 comprises an engagement feature configured to be used in combination with a compression clamp.

In addition to an annular engagement groove 518 and the recess 502, the head 510 of the reduction fastener includes a shoulder. For example, FIG. 5 illustrates that the head 510 comprises a rounded shoulder 516 that tapers along its length towards the shaft 512. The rounded shoulder 516 is configured to mate with the counterbore 118 (FIG. 1A) of an elongated slide channel 116 of a bone plate 100. More particularly, the rounded shoulder 516 is configured to allow the reduction fastener 500 to be pulled along the counterbore 118 (FIG. 1A) of an elongated slide channel 116.

As a fastener, the reduction fastener 500 includes threads that facilitate advancement of reduction fastener 500 into, and secures the reduction fastener 500 to, bone, tissue, or other material. For example, FIG. 5 illustrates that the shaft 512 of the reduction fastener 500 includes a single thread 522 that forms a spiral pattern extending from the head 510 to the tip 514 of the reduction fastener 500. In alternative implementations the shaft 512 includes a plurality of threads 522. In any event, the threads 522 are configured to engage bone, tissue, or other material and help the reduction fastener 500 advance therein.

In one or more implementations of the present invention, the reduction fastener 500 is self-starting and self-tapping. For example, FIG. 5 illustrates that the tip 514 of the reduction fastener 500 includes one or more flutes or teeth 524. The flutes 524 extend at least partially along the shaft 512, thereby dividing the proximal threads 522 of the shaft 512 into two or more sections. One will appreciate that the threads 522 are configured to be utilized with the flutes 524 to facilitate self-tapping of the reduction fastener 500 into the material into which it is to be inserted. For example, the flutes 524 are configured to cut a path into which the threads 522 follow.

In some implementations the reduction fastener 500 can include a partial or full cannula. The cannula can comprise a channel extending from tip 514 to head 510 along the length of the reduction fastener 500. The cannula can accommodate a thread, suture, guidewire or similar filament or other member permitting a practitioner to insert reduction fastener 500 to a desired position in a patient.

Figure 6:
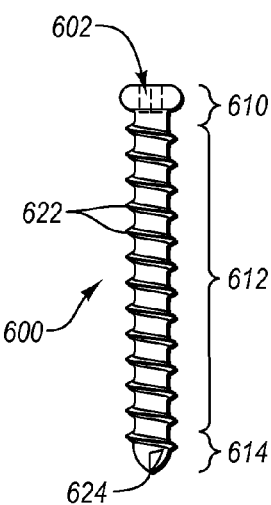
FIG. 6 illustrates a side perspective-view of a fixation fastener in accordance with an implementation of the present invention.

In addition to reduction fasteners 500, one or more implementations of a kit of the present invention may also include one or more fixation fasteners. The fixation fasteners may generally comprise any mechanism for affixing a bone plate to a bone, including screws, pins, and wires, among others. As shown in FIG. 6, in one implementation the fixation fastener comprises a bone screw 600. For example, FIG. 6 illustrates an exemplary fixation fastener 600, including a head 610, a shaft 612 with threads 622 extending along at least a portion thereof, and a tip 614.

In some implementations, the fixation fastener 600 is configured as a unicortical or bicortical bone screw, and thus, has relatively small threads 622 for use in hard bone, such as typically found in the shaft portion of a bone. In alternative implementations, the fixation fastener 600 is configured as a cancellous bone screws and has relatively larger threads for use in soft bone, such as typically found near the ends (periarticular regions) of a bone.

As a fastener, the threads 622 of the fixation fastener 600 facilitate advancement of fixation fastener 600 into, and secure the fixation fastener 600 to, bone, tissue, or other material. For example, FIG. 6 illustrates that the shaft 612 of the fixation fastener 600 includes a single thread 622 that forms a spiral pattern extending from the head 610 to the tip 614 of the fixation fastener 600. In alternative implementations the shaft 612 includes a plurality of threads 622. In any event, the threads 622 engage bone, tissue, or other material and help the fixation fastener 600 advance therein.

While FIG. 6 shows the thread 622 of the fixation fastener 600 extending along the entire length of the shaft 612, the present invention is not so limited. As such, in alternative implementations, the threads 622 extend along only a portion of the length of the shaft 612. For example, in some implementations the shaft 612 includes an un-threaded portion proximate the head 610.

In one or more implementations of the present invention, the fixation fastener 600 is self-starting and self-tapping. For example, FIG. 6 illustrates that the tip 614 of the reduction fastener 600 includes one or more flutes or teeth 624. The flutes 624 extend at least partially along the shaft 612, thereby dividing the proximal threads 622 of the shaft 612 into two or more sections. One will appreciate that the threads 622 are configured to be utilized with the flutes 624 to facilitate self-tapping of the reduction fastener 600 into the material into which it is to be inserted.

Furthermore, as FIG. 6 shows, the head 610 includes a recess 602 configured to receive a portion of a rotational tool, such as, for example, a drill or screw driver. More specifically, the recess 602 comprises a void into which a portion of a rotation tool can be inserted. One will appreciate that the rotational tool may provide the force necessary to rotate the fixation fastener 600 into a portion of bone or other material. As will be appreciated by those skilled in the art, the recess 602 can comprise a variety of types and configurations, such as those described above with relation to the recess 502 of the reduction fastener 500, without departing from the scope and spirit of the present invention.

Additionally, similar to the reduction fastener 500, in some implementations the fixation fastener 600 can include a partial or full cannula. The cannula can comprise a channel extending from tip 614 to head 610 along the length of the fixation fastener 600. The cannula can accommodate a thread, suture, guidewire or similar filament or other member permitting a practitioner to insert reduction fastener 600 to a desired position in a patient.

As explained in greater detail below, the fixation fastener 600 is configured to be inserted within a fixation hole 110, 112, 114 and/or an elongated slide channel 116 of a bone plate 100 to facilitate securement of the bone plate 100 to a portion of bone. Furthermore, in one or more implementations, the fixation fastener 600 is configured to lock into a fixation hole 110, 112, 114 of a bone plate 100. For example, the threads 622 of the fixation fastener 600 are configured to lock into the threads of a fixation hole 110, 112, 114.

Figure 7:
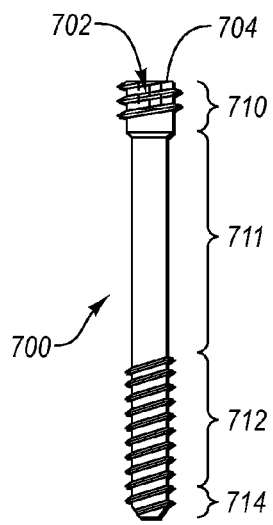
FIG. 7 illustrates a side perspective-view of a compression fastener in accordance with an implementation of the present invention.

In addition to the fasteners described herein above for use in combination with a bone plate, one or more implementations of a kit of the present invention includes one or more additional fasteners for providing additional compression of a bone discontinuity separately from a bone plate. For example, FIG. 7 illustrates a side perspective-view of an exemplary compression fastener 700. As shown in FIG. 7, the compression fastener 700 is headless. The headless configuration of the compression fastener 700 allows for distal end 704 of the compression fastener 700 to be placed in a substantially flush configuration with the outer surface of a bone into which the compression fastener 700 is inserted. Thus, the headless configuration of the compression fastener 700 reduces discomfort for the patient.

As shown by FIG. 7, the compression fastener 700 comprises a distal threaded portion 710, an un-threaded portion 711, a proximal threaded portion 712, and a tip 714. To aid in generating compression, the proximal thread portion 712 of the compression fastener 700 are configured to advance faster than distal threaded portion 710, thereby allowing for compression of a bone discontinuity along the un-threaded portion 711 of the compression fastener 700. For example, in one or more implementations of the present invention, the pitch of the threads of the distal threaded portion 710 are smaller than the pitch of the threads of the proximal threaded portion 712, thereby causing the proximal threaded portion 712 to advance quicker than the distal threaded portion 710. In addition, or alternatively, the angle of the threads of the proximal threaded portion 712 is greater than the angle of the threads of the distal threaded portion 710, thereby causing the proximal threaded portion 712 to advance quicker than the distal threaded portion 710.

Furthermore, as FIG. 7 shows, the distal end 704 of the compression fastener 700 includes a recess 702 configured to receive a portion of a rotational tool, similar to the recesses 502 and 602 described herein above in relation to the reduction fastener 500 (FIG. 5) and the fixation fastener 600 (FIG. 6). Additionally, in some implementations the compression fastener 700 can include a partial or full cannula. The cannula can comprise a channel extending from tip 714 to the distal end 704 along the length of the compression fastener 700. The cannula can accommodate a thread, suture, guidewire or similar filament or other member permitting a practitioner to insert compression fastener 700 to a desired position in a patient.

Figure 8A:
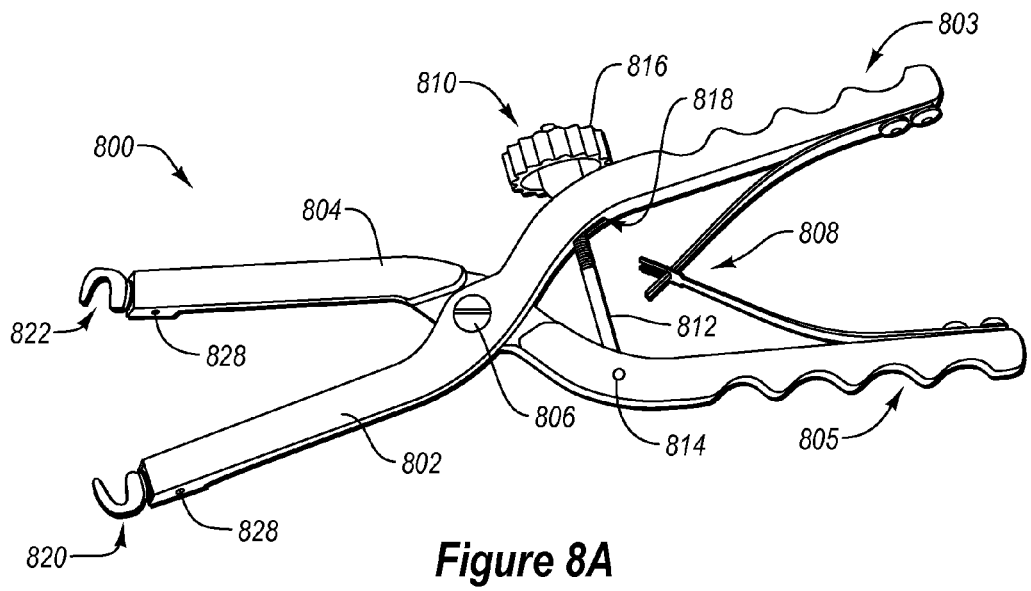
FIG. 8A illustrates a top perspective-view of a compression clamp in accordance with an implementation of the present invention.
Figure 8B:
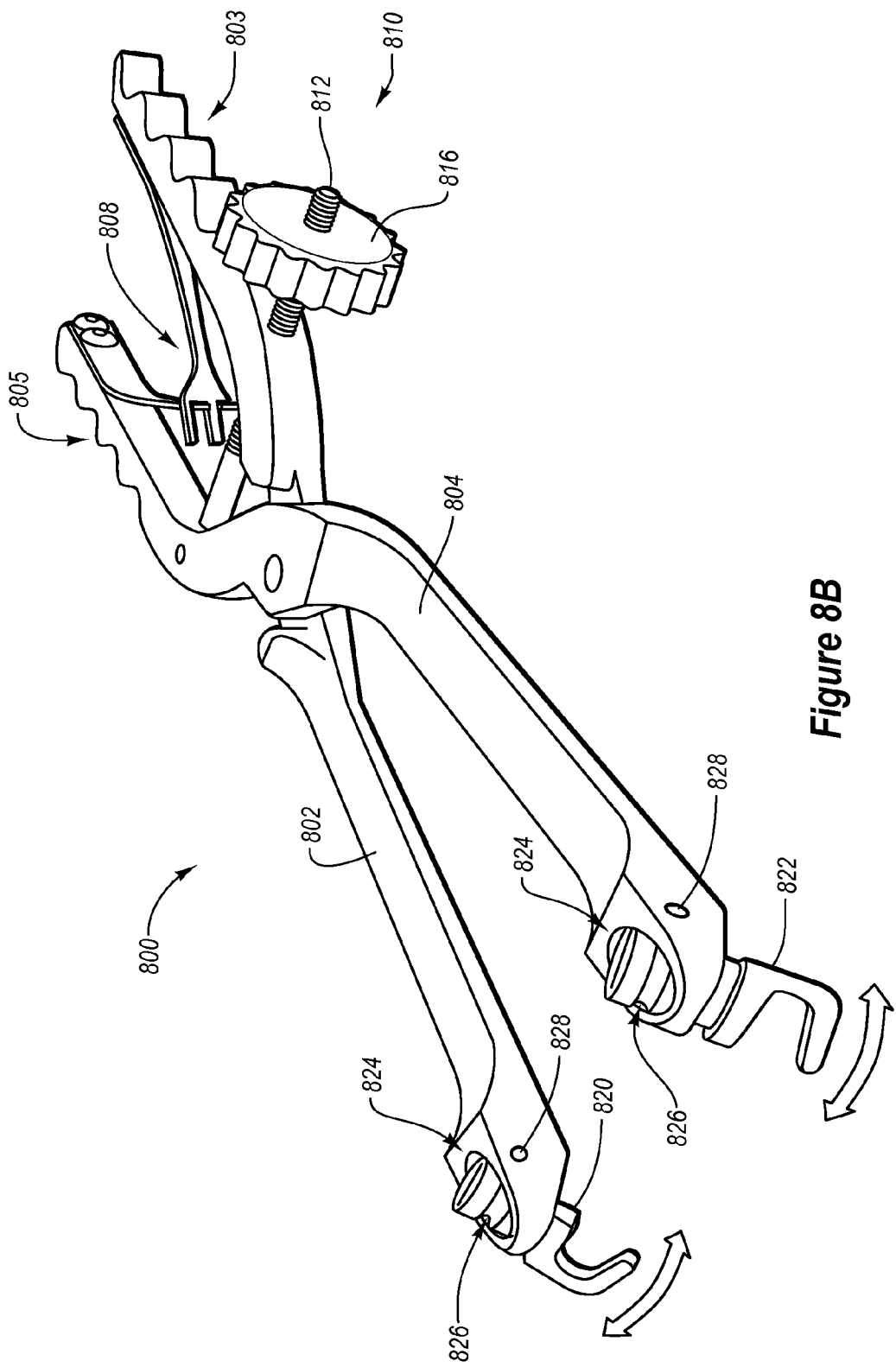
FIG. 8B illustrates a bottom perspective-view of the compression clamp of FIG. 8A.

Referring now to FIGS. 8A-8B, an exemplary compression clamp 800 of a kit of one or more implementations of the present invention is illustrated. As shown by FIG. 8A, the compression clamp 800 comprises a first lever 802 secured to a second lever 804 via a pivot 806. Each of the levers 802 includes a first end having a handle 803, 805, and a second end having an engagement member 820, 822. Furthermore, the compression clamp 800 include a biasing mechanism 808 configured to bias the ends of the first lever 802 away from the ends of the second lever 804. Thus, to close the compression clamp 800, or in other words draw the first engagement members 820, 822 toward each other, a user squeezes the handles 803, 805 of the first and second levers 802, 804 together.

The compression clamp 800 further includes a locking mechanism 810 configured to lock the positions of the engagement members 820, 822 relative to each other in one or more directions. For example, FIG. 8 illustrates that one implementation of a locking mechanism 810 of a compression clamp 800 includes a threaded rod 812 and a lock nut 816. More specifically, FIG. 8 illustrates that the threaded rod 812 is secured to the second lever 804 via a pivot 814, and extends through a slot 818 in the first lever 802. To lock the compression clamp 800, a practitioner translates the lock nut 816 along the threaded rod 812 until it engages the first lever 802, thereby preventing the compression clamp 800 from opening.

As mentioned previously, the compression clamp 800 includes a pair of engagement members 820, 822 configured to engage a head 510 of a reduction fastener 500 (FIG. 5). For example, FIG. 8 illustrates that in at least one implementation, the engagement members 820, 822 comprise hooks. The hooks 820, 822 are sized and configured to be inserted within an engagement groove 518 and around a neck 520 of a reduction fastener 500 (FIG. 5). In alternative implementations, the engagement members 820, 822 comprise rods sized and configured to be inserted within an engagement slot formed within the head 510 of a reduction fastener 500, or within a recess 502 of a reduction fastener 500.

In any event, in at least one implementation of the present invention, the engagement members 820, 822 are pivotally secured to the levers 802, 804 of the compression clamp 800. For example, FIG. 8B illustrates that the engagement members 820, 822 are secured within a respective hole 824 in the respective levers 802, 804. Thus, the engagement members 820, 822 are adapted to swivel or pivot within the holes 824 relative to the compression clamp 800, as illustrated by the arrows in FIG. 8B.

Furthermore, in some implementations of the present invention, the engagement members 820, 822 are configured to pivot within a limited range of motion. For example, FIG. 8B illustrates that each engagement members 820, 822 includes a first channel 826 extending into a first side thereof. Additionally, each engagement member 820, 822 includes a second channel (not shown) extending into an opposing side thereof. Furthermore, each lever 802, 804 includes a pivot pin 828 extending within the second channel. The second channel provides each engagement member 820, 822 with a limited range of pivoting motion. In particular, as an engagement member 820, 822 is pivoted within hole 824 in a first direction, one side of the second channel will eventually engage the pivot pin 828, thereby preventing further pivoting in the first direction. Similarly, as an engagement member 820, 822 is pivoted within hole 824 in a second direction, an opposing side of the second channel will eventually engage the pivot pin 828, thereby preventing further pivoting in the second direction.

One will appreciate that the amount of pivoting motion of the engagement members 820, 822 is dictated by the depth that the second channel extends into and around the engagement members 820, 822. The more the second channel extends around and into the engagement member 820, the greater the range of motion allowed before the second channel engages the pivot pin 828. In some implementations of the present invention, the engagement members 820, 822 are allowed to swivel or pivot within the holes 824 up to approximately ninety degrees. In additional implementations of the present invention, the engagement members 820, 822 are allowed to swivel or pivot within the holes 824 between an approximately five degree range and an approximately thirty-degree range of motion. In further implementations of the present invention, the engagement members 820, 822 are allowed to swivel or pivot within the holes 824 through an approximately fifteen-degree range of motion.

The pivotal connection to the levers 802, 804 allows the engagement members 820, 822 to pivot relative to the compression clamp 800, about the head 510 of the reduction fastener 500. One will appreciate in light of the disclosure herein that the pivoting of the engagement members 820, 822 allows for compensation of height, angle, and other various misalignments of the reduction fasteners 500 due to complications inherent in surgery, difference in surface contours of the bone portions of a bone discontinuity, or other real world circumstances. The limited range of motion provided to the engagement members 820, 822 ensures that engagement members 820, 822 do not pivot or swivel so much as to prevent or delay engagement with a reduction fastener 500 by becoming an additional source of misalignment.

In one or more implementations of the present invention, the surgical components described herein above are provided as a kit for use to repairing bone. One will appreciate that such a kit may include other conventional medical instruments, such as, for example, a scalpel, a saw, a drill and/or a screwdriver. The use of these elements in an exemplary surgical operation will now be described with reference to FIGS. 9-10F, which illustrate the repair of an exemplary bone discontinuity.

Figure 9:
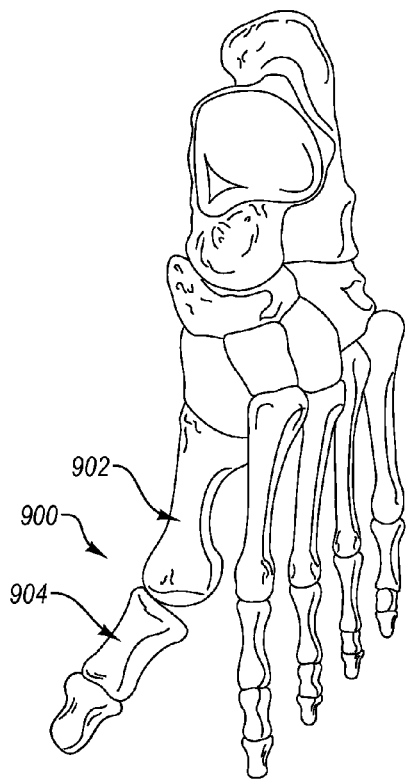
FIG. 9 illustrates a top perspective-view of an exemplary bone discontinuity, specifically a dislocation of a metatarsophalangeal joint.

Referring now to FIG. 9, an exemplary bone discontinuity, which a kit of the present invention may be used to correct, is shown. More specifically, FIG. 9 illustrates a dislocation 900 of the first metatarsophalangeal joint, or in other words, a dislocation of the first metatarsal bone 902 and the first proximal phalange 904. While the exemplary method described herein is in relation to the correction of a first metatarsophalangeal joint dislocation 900, one will appreciate that this is just one exemplary bone discontinuity that the kit, components, and methods of the present invention may be used to correct.

Indeed, by varying the type, shape, and number of bone plates, reduction fasteners, fixation fasteners, and/or compression fasteners, kits and components of the present invention can correct most, if not all, types of bone discontinuities. As used herein the term "bone discontinuity" refers to any separation of bone portions, whether the bone portions are separate bones or portions of the same bone. Furthermore, as used the term "bone portion" refers to both natural and artificial bone, such as implants. Thus, implementations of the present invention can be used to fuse bones together, correct fractures or clean breaks, graft segments of bone together, or otherwise draw two bone portions together.

The first step in one implementation of a method of the present invention includes prepping the bone discontinuity 900. In particular, a practitioner exposes the bone discontinuity. Depending on the type of bone discontinuity, prepping the bone discontinuity 900 further involves de-articulation between bones to be fused. For example, in the specific example of a dislocation 900 of the first metatarsophalangeal joint, prepping the bone discontinuity 900 involves de-articulation of the joint between the first metatarsal bone 902 and the first proximal phalange 904.

Figure 10A:
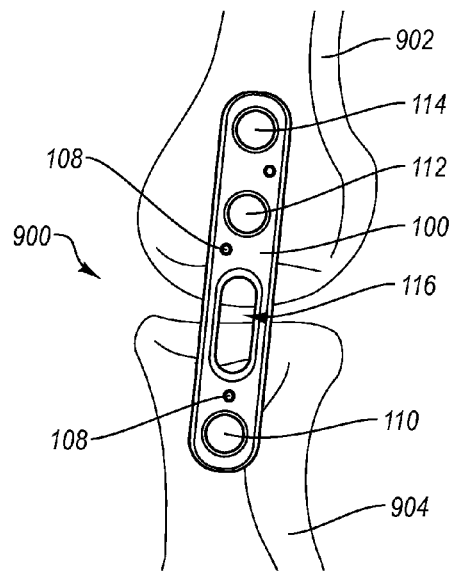
FIG. 10A illustrates the bone plate of FIGS. 1A-1B in an exemplary operating environment, depicting the bone plate placed about the exemplary bone discontinuity of FIG. 9 in accordance with an implementation of the present invention.

After prepping the bone discontinuity 900, or alternatively, prior to or in conjunction therewith, the practitioner selects a bone plate. For example, the type, shape of bone plate (e.g., linear, Y-shaped, T-shaped, butterfly shaped), length, and thickness of bone plate is selected based on the particular bone discontinuity. For example, FIG. 10A illustrates that a practitioner selects a linear bone plate 100 for use with the dislocation 900 of the first metatarsophalangeal joint.

In conjunction with selecting the bone plate 100, a practitioner may also contour, or otherwise shape, the bone plate 100 to correspond with the bone discontinuity 900 being corrected. For example, the practitioner may add dorsal curvature to the bone plate 100 by using a pair of bending pliers.

The method then involves placing the bone plate 100 adjacent the bone discontinuity 900. For example, FIG. 10A illustrates that a practitioner spans the bone plate 100 across the bone discontinuity 900. More specifically, the practitioner ensures that the elongated slide channel 116 extends over and across the bone discontinuity 900. Additionally, the practitioner ensures that at least one fixation hole 114, 112 is positioned above a first portion 902 of the bone discontinuity 900, and at least a second fixation hole 110 is positioned above a second portion 904 of the bone discontinuity 900.

Optionally, the method can include temporarily fixing the bone plate 100 about the bone discontinuity 900. For example, a practitioner secures the bone plate 100 to the bone discontinuity 900 by via a guide wire or K-wire through one or more of the attachment holes 108 of the bone plate 100 to the first portion 902 and/or the second portion 904 of the bone discontinuity 900.

Figure 10B:
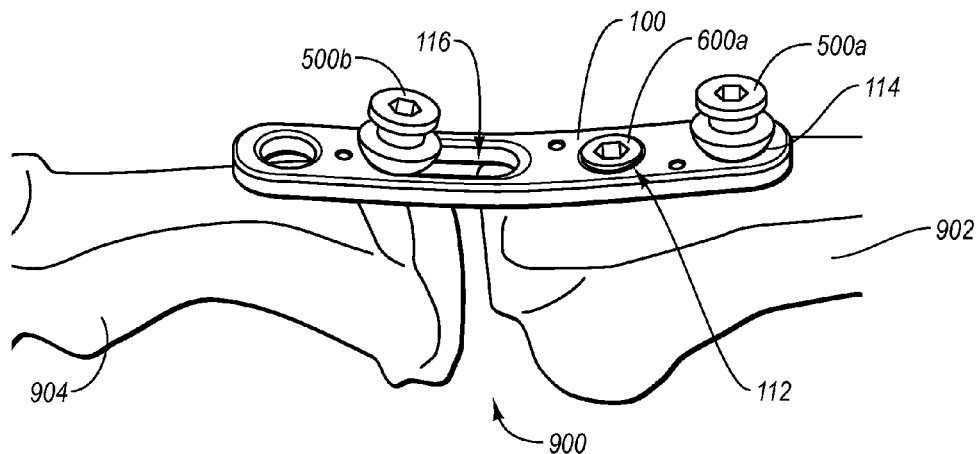
FIG. 10B illustrates the bone plate of FIG. 10A secured to the portions of the exemplary bone discontinuity via the fixation fastener of FIG. 6 and a pair of reduction fasteners of FIG. 5.

Referring now to FIG. 10B, the method involves securing a first reduction fastener 500a within a first fixation hole 114 of the bone plate 100 and to the first bone portion 902. One will appreciate that the first reduction fastener 500a can be secured to the first bone portion 902 in any number of ways. For example, in one implementation, a practitioner drills a pilot hole into the first bone portion 902, and then tightens the first reduction fastener 500a into the pilot hole of the first bone portion 902. Additionally or alternatively, when the first reduction fastener 500a comprises a cannula, the practitioner first places a guidewire within the first fixation hole 114 and into the first bone portion 902, and then tracks the first reduction fastener 500a along the guidewire and into the first bone portion 902. In yet further implementations, when the first reduction fastener 500a is self-tapping, the practitioner secures the reduction fastener 500a directly into the first bone portion 902 without the use of pilot hole or guidewire.

Along similar lines, the method also involves securing a second reduction fastener 500b within the elongated slide channel 116 of the bone plate 100 and to the second bone portion 904. One will appreciate that the second reduction fastener 500b can be secured to the second bone portion 904 in any of the ways described above with reference to securing the first reduction fastener 500a to the first bone portion 902.

The method optionally further involves securing a first fixation fastener 600a within a second fixation hole 112 of the bone plate 100 and to the first bone portion 902. One will appreciate that the first fixation fastener 600a can be secured to the first bone portion 902 in any number of ways. For example, in one implementation, a practitioner drills a pilot hole into the first bone portion 902, and then tightens the first fixation fastener 600a into the pilot hole of the first bone portion 902. Additionally or alternatively, when the first fixation fastener 600a comprises a cannula, the practitioner first places a guidewire within the second fixation hole 112 and into the first bone portion 902, and then tracks the first fixation fastener 600a along the guidewire and into the first bone portion 902. In yet further implementations, when the first fixation fastener 600a is self-tapping, the practitioner secures it directly into the first bone portion 902 without the use of pilot hole or guidewire.

Additionally, securing the fixation fastener 600a to the first bone portion 902 can optionally comprise angling the first fixation fastener 600a relative to the bone plate 100. For example, the practitioner angles the first fixation fastener 600a away from the bone discontinuity 900 or otherwise helps ensure that the first fixation fastener 600a is securely fastened to the first bone portion 902.

Figures 10C, 10D:
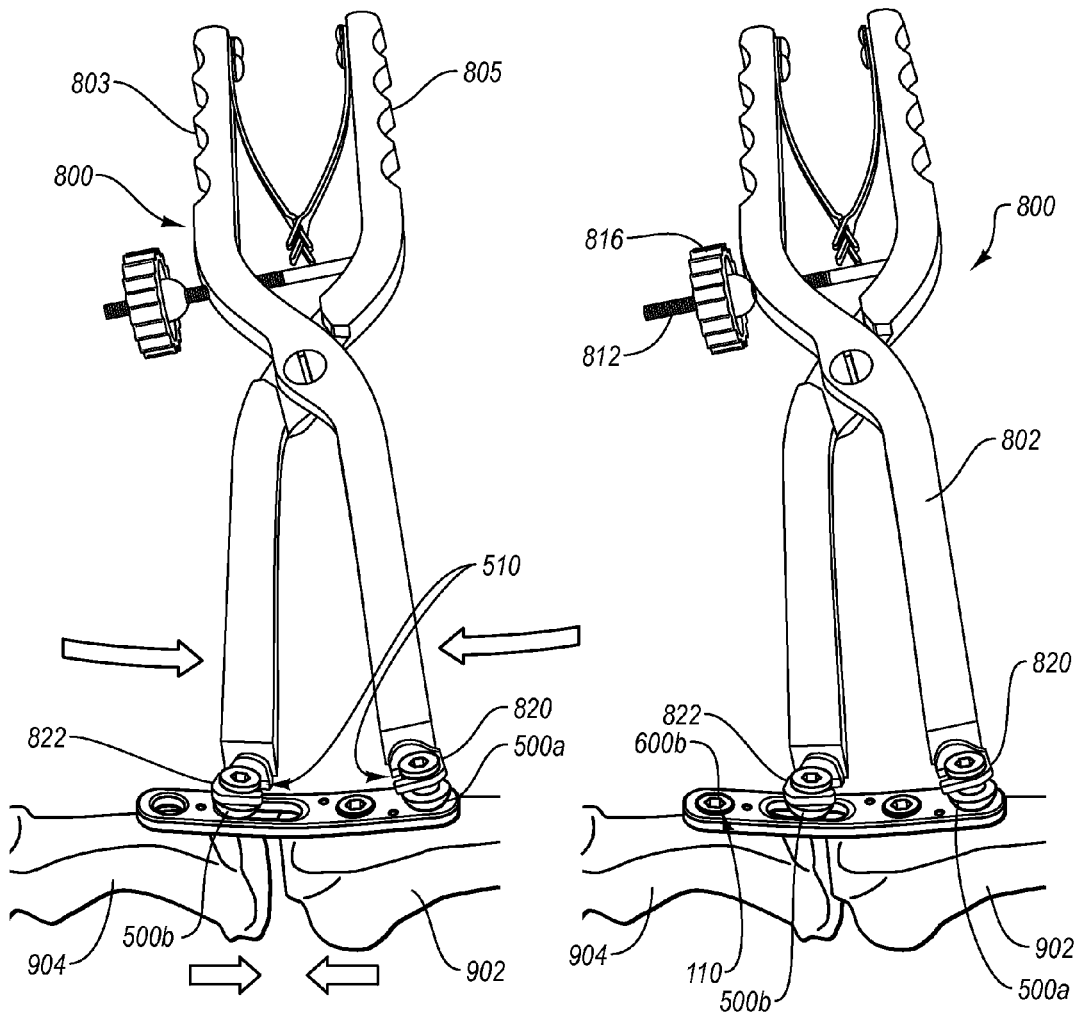
FIG. 10C illustrates the compression clamp of FIGS. 8A-8B placed about the reduction fasteners of FIG. 10B.
FIG. 10D illustrates the compression clamp of FIG. 10C in a locked configuration after the reduction fasteners of FIG. 10B have been compressed together to reduce the exemplary bone discontinuity.

As shown in FIG. 10C, one will appreciate that an implementation of a kit of the present invention includes a bone plate 100, a pair of reduction fasteners 500a, 500b, at least one fixation fastener 600a, and a compression clamp 800. As shown in FIG. 10C, the method further involves using the kit to compress the bone discontinuity 900. In particular, the method involves engaging the first and second reduction fasteners 500a, 500b with the compression clamp 800. Specifically, the practitioner positions a first engagement member 820 of the compression clamp 800 about the head 510 of the first reduction fastener 500a, and a second engagement member 822 of the compression clamp 800 about the head 510 of the second reduction fastener 500b. In at least one implementation of the present invention, positioning an engagement member 820, 822 about the head 510 of a reduction fastener 500 involves causing the engagement member 820, 822 to pivot relative to the compression clamp 800 and about the head 510 of the reduction fastener 500. One will appreciate in light of the disclosure herein that the pivoting of the engagement member 820, 822 can compensate for height, angle, and other various misalignments of the reduction fastener 500 due to complications inherent in surgery, difference in surface contours of the bone portions 902, 904, or other real world circumstances.

Alternatively, positioning the engagement members 820, 822 of the compression clamp 800 about the heads 510 of the reduction fasteners 500a, 500b involves inserting a hook 820 within an engagement groove 518 of reduction fastener 500 and about the neck 520 of the head 510 of the reduction fastener 500. In yet further implementations, the method can involve positioning an engagement rod within an engagement slot of the head 510 of the reduction fastener 500.

After having secured the engagement members 820, 822 of the compression clamp 800 about the reduction fasteners

500a, 500b, the method involves closing the compression clamp 800 thereby drawing the second reduction fastener 500b (and the second bone portion 904) along the elongated slide channel 116 toward the first reduction fastener 500a (and the first bone portion 902), thereby compressing the bone discontinuity 900. To close the compression clamp 800, the practitioner squeezes the handles 803, 805 together, thereby drawing the first engagement member 820 toward the second engagement member 822, as illustrated by the arrows in FIG. 10C. One will appreciate in light of the disclosure herein that compressing the bone discontinuity 900 by physically closing the compression clamp 800, the practitioner has the ability to manually control the amount of compression and/or manually adjust the osteotomy before final fixation of the bone plate 100.

As mentioned previously, the kit can thus allow a practitioner to not only manually control the compression and reduction of a bone discontinuity 900, but to also feel and/or see the amount of compression. The ability to feel and/or see the amount of compression allows the practitioner to properly set the spacing and alignment between bone portions 902, 904 of the bone discontinuity 900, and thereby help ensure proper healing. In other words, one or more implementations of a kit of the present invention provide a practitioner with physical or tactile feedback during the compression of the bone discontinuity 900, and thus, provide the practitioner with the ability to better control the compression and spacing of bone portions 902, 904 during a reduction.

After compressing the first bone portion 902 and the second bone portion 904 together as desired, the practitioner then locks the compression clamp 800. For example, FIG. 10D illustrates that the practitioner tightens the lock nut 816 against the first lever 802 of the compression clamp 800 by translating the lock nut 816 along the threaded rod 812. One will appreciate in light of the disclosure herein that locking the compression clamp 800 includes locking the position of the first engagement member 820, and thus the first reduction fastener 500a and first bone portion 902, relative to the second engagement member 822, and thus the second reduction fastener 500b and the second bone portion 904.

After locking the bone portions 902, 904 relative to each other, the practitioner secures a second fixation fastener 600b within a third fixation hole 110 of the bone plate 100 and to the second bone portion 904. One will appreciate that the second fixation fastener 600b can be secured to the second bone portion 904 in any of the ways described above with reference to securing the first fixation fastener 600a to the first bone portion 902.

Figure 10E:
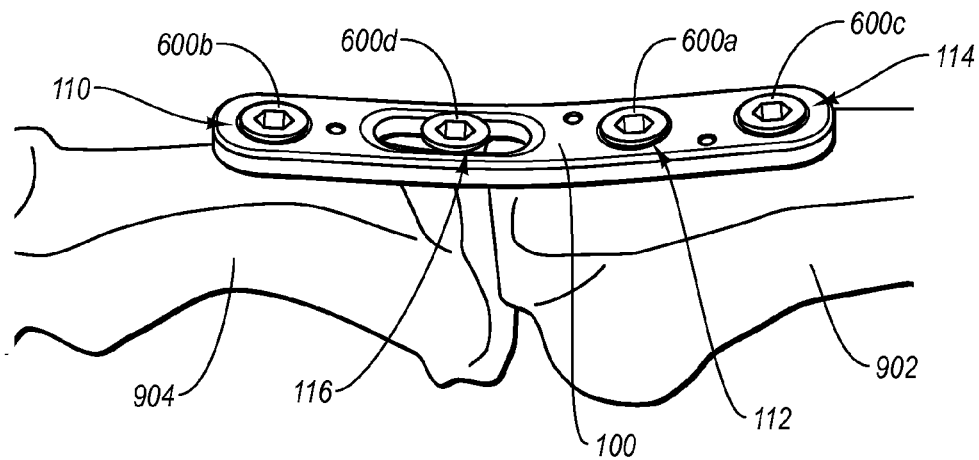
FIG. 10E illustrates the bone plate of FIG. 10A secured to the bone portions of the exemplary bone discontinuity, which have been aligned and compressed together.

With both the first and second fixation fasteners 600a, 600b secured within the fixation holes 110, 112 of the bone plate 100, and to the opposing bone portions 902, 904 of the bone discontinuity 900, the practitioner removes the compression clamp 800 and the first and second reduction screws 500a, 500b. Then as shown by FIG. 10E, the practitioner can optionally secure a third fixation fastener 600c within the first fixation hole 114 to the first bone portion 902 to provide additional fixation. Furthermore, the practitioner can also optionally insert a fourth fixation fastener 600d with the elongated slide channel 116 and to the second bone portion 904 to provide yet additional fixation of the bone discontinuity 900. One will appreciate that the third and fourth fixation fasteners 600c, 600d are inserted within the holes formed in the first and second bone portions 902, 904 formed by inserting the first and second reduction fasteners 500a, 500b repetitively therein.

Figure 10F:
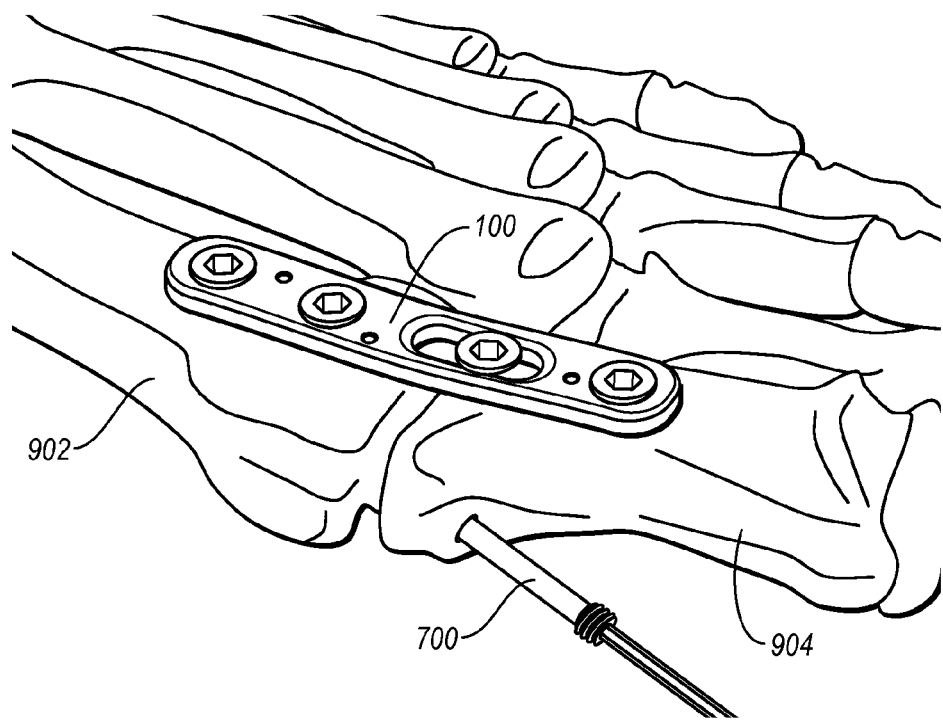
FIG. 10F illustrates a view of the compression fastener of FIG. 7 being inserted about the reduced exemplary bone discontinuity.

After having secured the bone plate 100 to the opposing bone portions 902, 904 of the bone discontinuity 900 via two or more fixation screws 600, the practitioner can optionally provide even further fixation to the bone discontinuity 900 by adding one or more additional fixation devices. For example, FIG. 10F illustrates that the practitioner secures compression fastener 700 into the first and second bone portions 902, 904 of the bone discontinuity 900.

Accordingly, one or more implementations of components, a kit, and methods described herein provide a practitioner with a great deal of functional versatility in repairing bone discontinuities. Furthermore, as discussed herein, the components, kit, and methods of one or more implementations of the present invention allow for efficient and accurate correction of various different types of bone injury by allowing a practitioner to manually control the compression and reduction of a bone discontinuity, while receiving physical feedback on amount of compression.

FIGS. 12, 13, 14, and 19 show additional embodiments of clamps of the present invention that may be configured in a manner similar to clamp 800, except that the engagement members of the clamps 1000, 1020, 1040, and 1100 have different mounting portions for mounting on a reduction fastener, such as the mounting portions having oval apertures of engagement members 1006, 1008 of clamp 1000.

Figure 12:
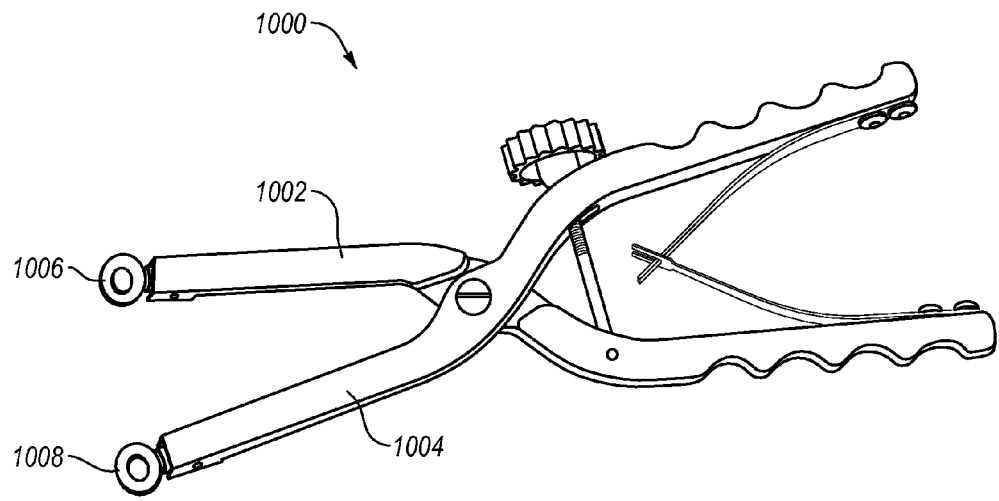
FIG. 12 illustrates a perspective view of another compression clamp in accordance with an implementation of the present invention, the compression clamp having engagement members with oval-shaped apertures extending therethrough (the apertures may optionally be circular shaped)

With reference now to FIG. 12, compression clamp 1000 is shown. Compression clamp 1000 comprises first and second levers 1002 and 1004 movably coupled to each other. Engagement members 1006, 1008 are pivotally coupled to respective engagement members 1002, 1004. Such pivotal coupling may be in the same or a similar manner as described with respect to compression clamp 800 and in the discussion of FIGS. 8A-10D and the specifications relating thereto, for example.

Engagement members 1006, 1008 each have an oval-shaped, apertures extending therethrough for selective mounting on oval shaped reduction fasteners. The oval shaped apertures of engagement members 1006, 1008 are designed for placement on corresponding reduction fasteners, which may be in the form of screws, pins, wires, bits, and other reduction fasteners, for example.

In another implementation, the engagement members 1006, 1008 may have circular apertures extending therethrough. However, the apertures of the engagement members of the clamps of the present invention may be square, rectangular, hexagonal, or a variety of other shapes, for mounting on corresponding reduction fasteners, for example.

Figure 13:
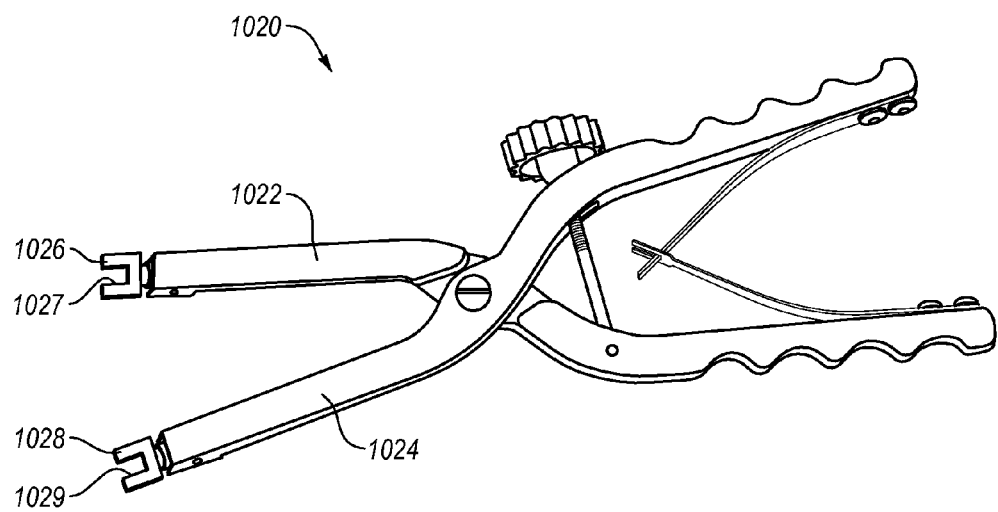
FIG. 13 is yet another implementation of a compression clamp of the present invention, the compression clamp having U-shaped engagement members.

Similarly, with respect to FIG. 13, compression clamp 1020 has movably coupled levers 1022, 1024 having respective engagement members 1026, 1028 pivotally coupled thereto. Engagement members 1026 and 1028 each have a U-shaped mounting portion 1027, 1029 which is selectively mounted on a square or rectangular-shaped reduction fastener, for example.

Figure 14:
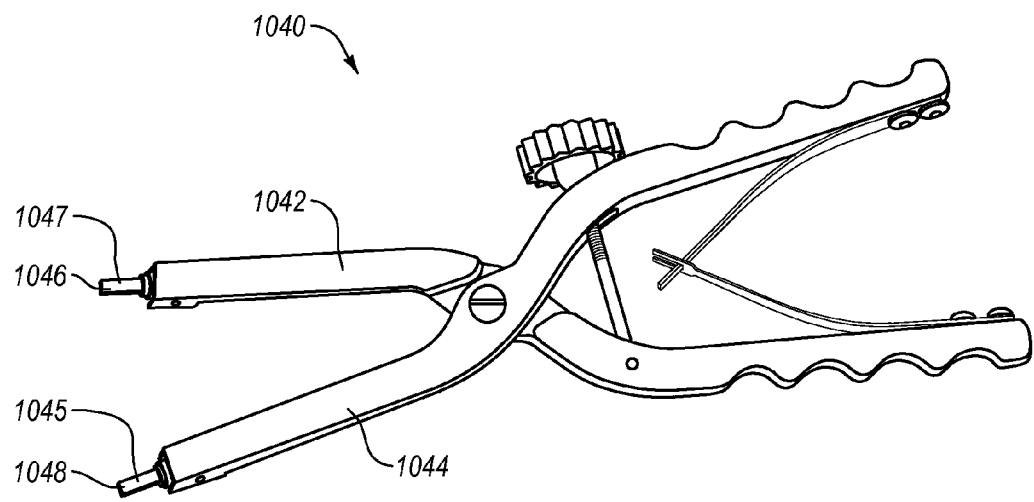
FIG. 14 illustrates another implementation of a compression clamp of the present invention, the compression clamp having engagement members, each engagement member having a square shaped post.
Figure 15:
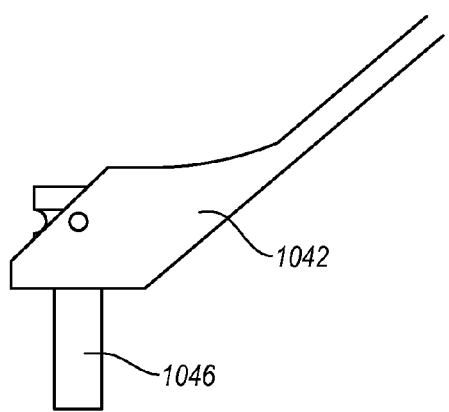
FIG. 15 illustrates a side cut-a-way view of a portion of the compression clamp of FIG. 14, showing the square-shaped post of the engagement member.

Yet another clamp 1040 is shown in FIGS. 14 and 15. Clamp 1040 comprises first and second levers 1042, 1044 having respective engagement members 1046, 1048 pivotally coupled thereto, wherein the mounting portions 1047, 1045 of respective engagement members 1046 and 1048 comprise posts having a square cross-sectional shape so as to mount within the head of a reduction fastener, such as the reduction fastener 1060 of FIG. 16, for example. The post-shaped mounting portions 1047, 1045 of respective engagement members 1046 and 1048 can optionally have a round or circular cross section, for example.

Figure 16:
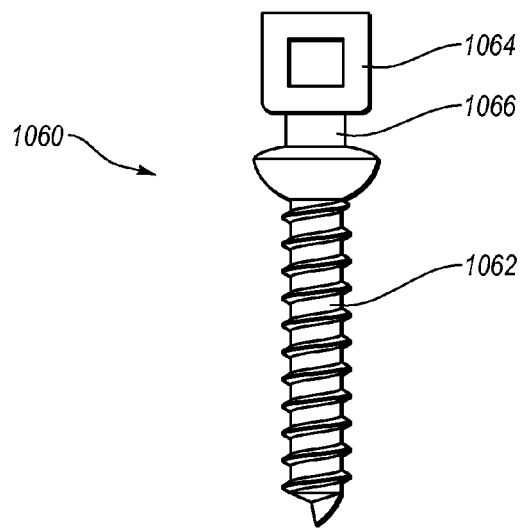
FIG. 16 is a front view of a reduction fastener of the present invention, the reduction fastener having a head portion with one or more rectangular apertures extending therethrough (configured, for example, to receive the post of FIGS. 14-15)

FIG. 16 illustrates a reduction fastener 1060 having a square-shaped aperture in the head 1064 thereof that is configured to receive one of the engagement members 1046, 1048 of clamp 1040. Fastener 1060 may receive engagement members 1046, 1048 from either a front or side insertion direction, and/or in one implementation, within a recess formed in the top portion of the head 1064 of fastener 1060. A similar square-shaped hole to that shown in FIG. 15 may extend through the sides of the head 1064 of fastener 1060. Fastener 1060 comprises a head 1064 having neck 1066. Head 1064 is coupled to a threaded shaft 1062.

Figures 17, 18:
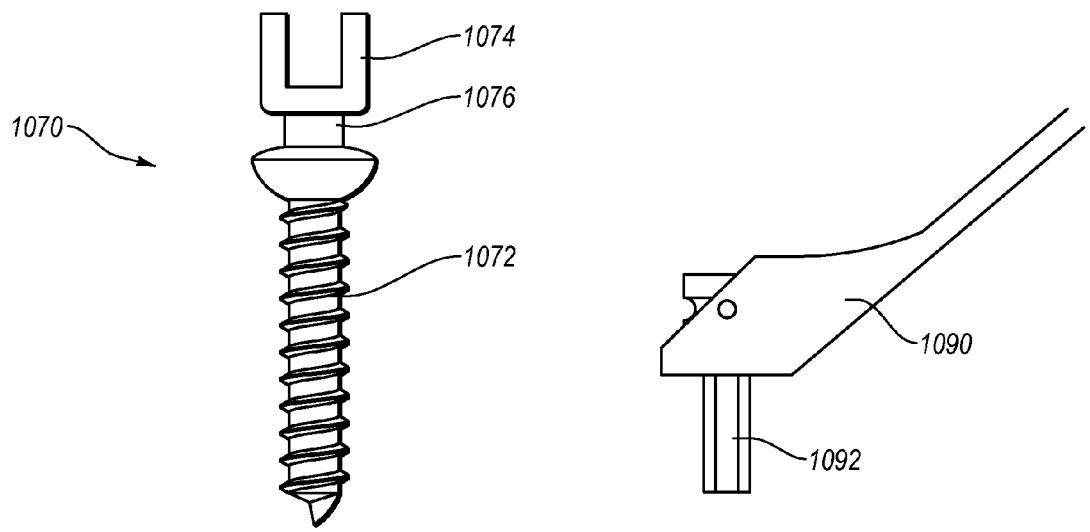
FIG. 17 illustrates yet another implementation of reduction fastener of the present invention, the reduction fastener having a U-shaped head portion that is configured to receive the post of an engagement member of the compression clamp of FIG. 14, for example.
FIG. 18 illustrates a side cut-a-way view of a portion of a compression clamp in accordance with another implementation of the present invention, illustrating a hexagonal post of an engagement member for example.

FIG. 17 shows an optional reduction fastener 1070 of the present invention, that can also receive one of the engagement members of clamp 1040 of FIG. 14, for example, reduction fastener 1070 having a threaded shaft 1072 coupled to a U-shaped head portion 1074, which includes neck portion 1076. U-shaped head portion 1074 can have a U-shaped cross section in a front to back direction, as shown, and/or in a side to side direction, for example.

With reference now to FIG. 18, an additional example of an engagement member 1092 for connection on any of the levers of the compression clamps described herein, or similar levers, is now shown. FIG. 18 shows a lever 1090 of a compression clamp having an engagement member 1092 pivotally coupled thereto, the engagement member having the form of a hex-shaped post. Thus, the clamps and engagement members of the present invention can have a variety of different shapes and configurations that accomplish the goals of the present invention.

Figure 19:
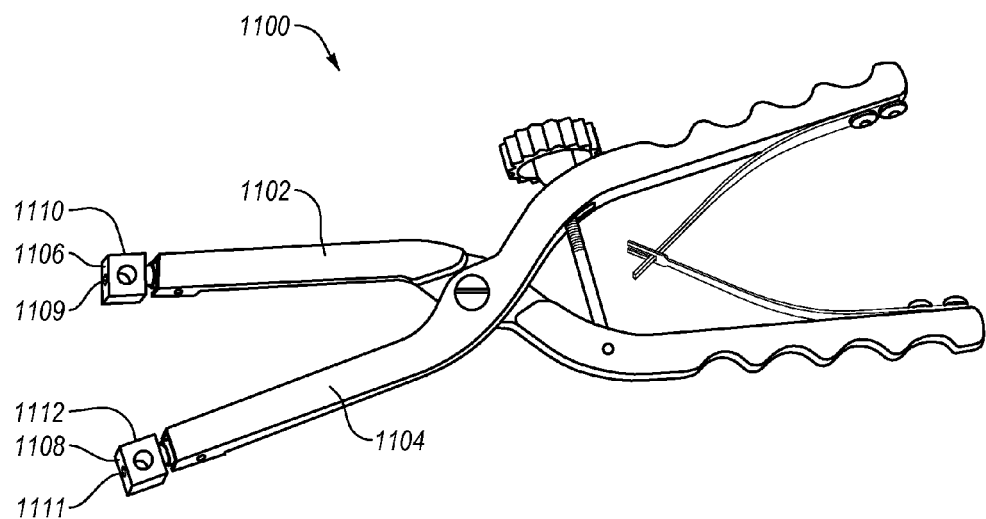
FIG. 19 is yet another example of a compression clamp of the present invention having engagement members, with a circular aperture therethrough, which are designed to be selectively, slidably, mounted on the reduction fasteners of FIGS. 20 and 20a, for example.
Figures 21, 22:
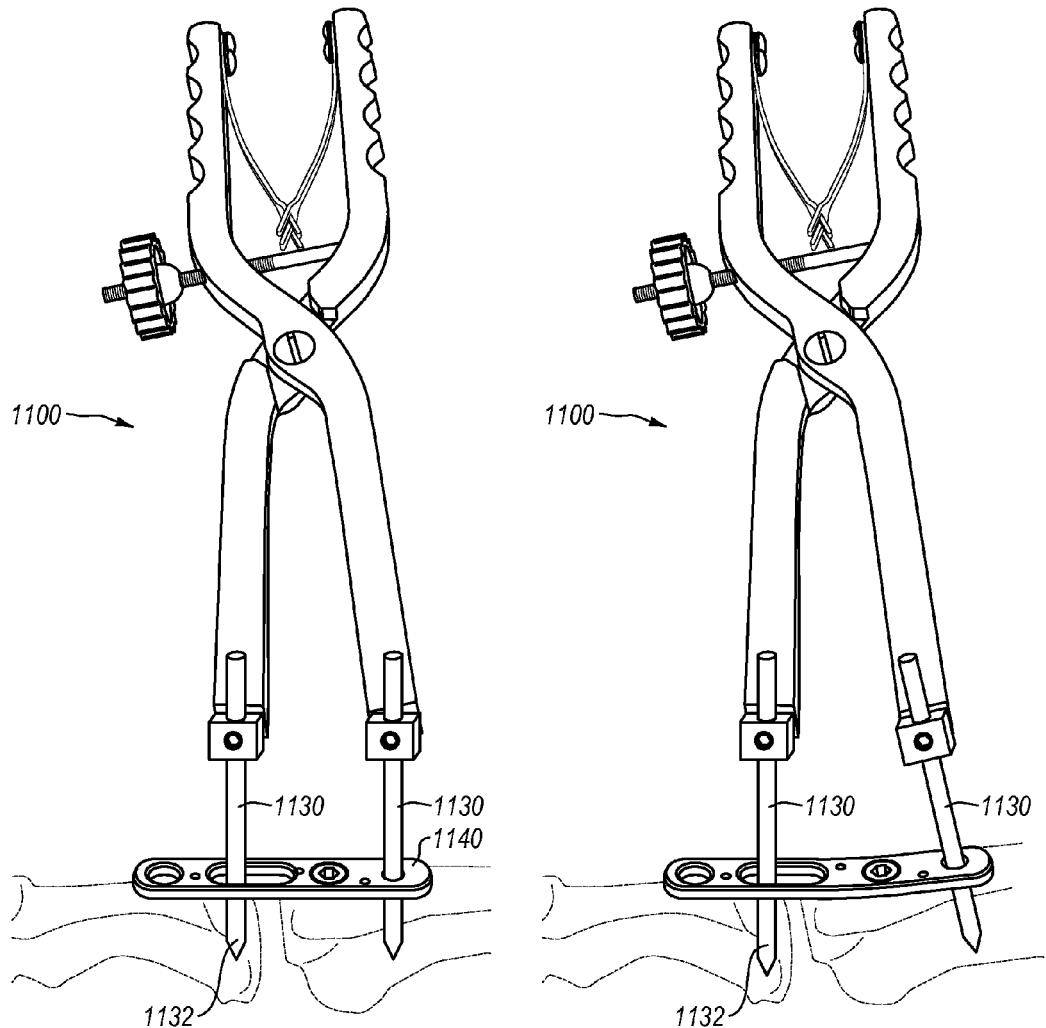
FIGS. 21 and 22 illustrate the compression clamp of FIG. 19 mounted on elongate reduction fasteners in the form of unthreaded elongate pins inserted through bone plates and mounted within bone fragments.

FIGS. 19, 21 and 22 illustrate another example of a compression clamp 1100 of the present invention. Clamp 1100 has movably coupled levers 1102 and 1104 having respective engagement members 1106 and 1108 pivotally coupled thereto. Such pivotal coupling mechanism may be the same as or similar to that described in connection with clamp 800, for example.

The engagement members each comprise a respective mounting chamber 1110, 1112 having a circular aperture extending therethrough. The mounting chamber 1110, 1112 can be selectively slid over a desired reduction fastener, or a slidably receive a reduction fastener therein.

Connectors such as set screws 1109, 1111 are positioned within respective mounting chambers 1110, 1112 of engagement members 1106, 1108 and threadably positioned against a desired reduction fastener such that engagement members 1106, 1108 can be firmly coupled to a desired reduction fastener, such as pin or screw, so as to provide additional leverage and grip to manipulate the fastener into a desired position. However, in another embodiment, connectors such as set screws are not employed, the practitioner relying upon the friction fit created by the twisting force to maintain the reduction fastener in a desired position with respect to an engagement member.

Figure 20:
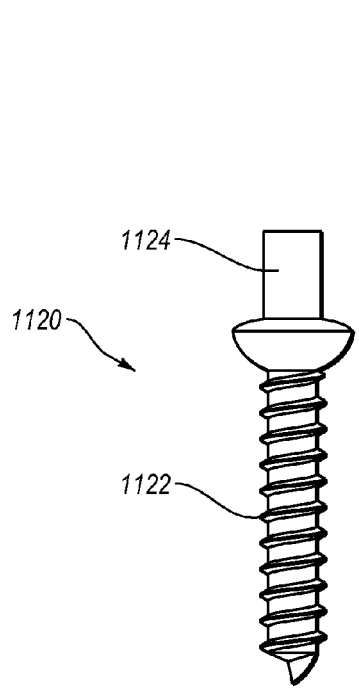
FIGS. 20 and 20a represent reduction fasteners in accordance with implementations of the present invention.
Figure 20A:
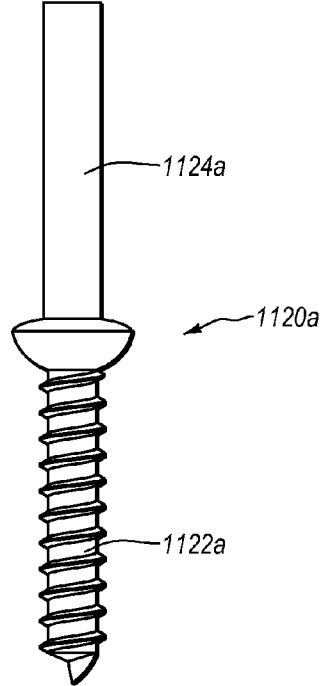

Engagement members 1106, 1108 are selectively mounted on and selectively engage reduction fasteners in the form of elongate screws, pins, wires, rods, or drill bits having a circular cross section, such as screws 1120, 1120a shown in FIGS. 20, 20a and/or elongate pins 1130 shown in FIG. 21, for example.

Furthermore, through the use of a mounting chamber 1110 that surrounds a reduction fastener (see FIGS. 21-22a), a particular reduction fastener can be moved to the right or the left side as required for a particular adjustment.

Engagement members 1106, 1108 have circular shaped apertures in the mounting portions thereof, but may optionally have a variety of different shaped apertures, e.g., square, or hex shaped apertures, for example. Nevertheless, the circular shaped apertures enable the engagement members 1106, 1108 to be conveniently, selectively mounted along circular shaped reduction fasteners or slidably receive the circular reduction fasteners from a variety of different positions. Since they are circular shaped, the apertures can enable the mounting onto the reduction fasteners without having to (i) reorient the reduction fasteners in order to correspond to the shape of the apertures of engagement members 1106, 1108, or (ii) reorient the engagement members 1106, 1108 in order to correspond to the shape of the apertures of the reduction fasteners, as may occur when other shapes, e.g., square apertures are employed.

For example, clamp 1100 can be selectively mounted on and engage reduction fastener screws 1120, 1120a, for example, from a variety of different angles, such that screws 1122, 1122a can be selectively compressed and manipulated for purposes of reduction of adjacent bone discontinuities.

Screws 1120 and 1120a shown in respective FIGS. 20 and 20a each include a threaded shaft 1122, 1122a coupled a head portion 1124, 1124a having a circular cross sectional configuration, such that engagement members 1106 and 1108 of clamp 1100 can be selectively mounted thereon. Screws 1120, 1120a may have a recess in the top portion thereof configured to enable screws 1120, 1120a to be positioned in a desired position in a bone through the use of a rotational screw driving tool or drill, for example.

Figure 22A:
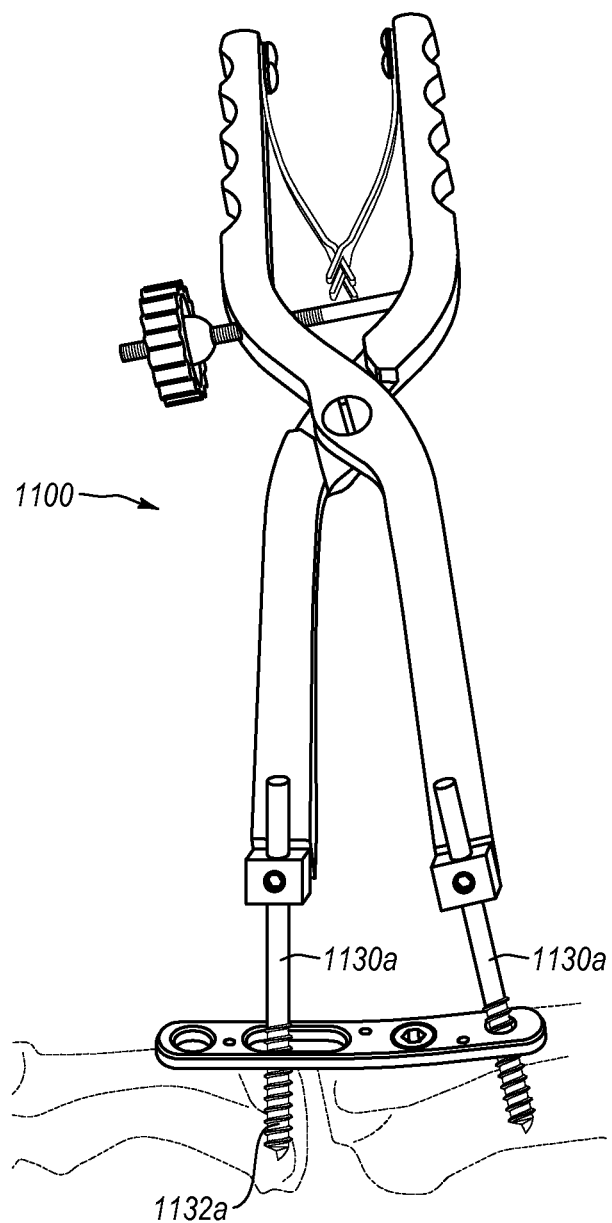
FIG. 22a illustrates the compression clamp of FIG. 19 mounted on elongate reduction fasteners in the form of threaded screws.

Examples of a use of clamp 1100 mounted on alternative reduction fasteners in the form of pins 1130 or screws 1130a are shown in FIGS. 21-22a, for example. As shown, the elongate reduction fastener pins 1130 and/or reduction fastener screws 1130a are selectively placed through the appropriate apertures in a bone plate 1140 of the present invention and into respective bone portions, after which clamp 1100 is selectively mounted thereon as shown in FIG. 21, for the purpose of compression and repositioning the bone fragments with respect to each other. Optionally, the reduction fasteners can first be placed within clamp 1100, then mounted through plate 1140 within respective bone fragments.

When desired, clamp 1100 can be compressed such that the bone fragments are compressed with respect to each other. The circular shaped apertures of engagement members 1106, 1108 conveniently fit onto the elongate pins 1130 or screws 113a.

Advantageously, as shown in FIGS. 21-22a, bone portions can be readily manipulated by employing elongate reduction fasteners in the form of screws and/or pins that extend high above the bone plate such that additional leverage is available to move the bone discontinuities with respect to each other. Elongate pins 1130, and screws 1130a are examples of the use of such longer reduction fasteners.

The additional leverage provided by the longer pins/screws allows for finer tuning of the position of a bone and allows a bone fragment to be tilted one way or another such that the portions of bone can ultimately be brought together into a desired alignment. Through use of clamp 1100, one bone fragment can be manipulated independently from the other.

For example, FIG. 22 illustrates that one lever of clamp 1100 can be moved from the position of FIG. 21, thereby tilting a bone fragment, as shown by the slightly tilted fragment on the right side of FIG. 22. FIGS. 21-22 thus illustrate that bone discontinuities can be fine tuned and tilted with respect to each other as desired when employing a combination of clamp 1100 and elongated reduction fasteners. FIG. 22a illustrates the use of screws 1130a as reduction fasteners. In one embodiment, bone plate 1140 is first bent independently from clamp 1100, after which the positions of one or more bone fragments are adjusted.

As part of the ability to fine tune a fracture, the use of elongated pins 1130 and/or elongated screws 1130a enables a practitioner to reduce, i.e., compress, both the top portion of a bone fragment and the bottom portion of a bone fragment. Since the practitioner has the leverage to tilt the bone fragment up or down, for example, the practitioner can adjust the position of the bone fragment such that both the top portion of the fragment and the bottom portion of the fragment move to a desired position with respect to an adjacent fragment. Thus, the use of clamp 1100 and elongate pins and/or screws can be useful in providing appropriate alignment of both the top and bottom portions of the bone fragments.

Furthermore, by employing a clamp 1100 having engagement members 1106, 1108 with a mounting chamber that surrounds a respective reduction fastener, as shown in FIGS. 21-22a, clamp 1100 can be employed to move a selected reduction fastener into one direction or another. Thus, fasteners 1130, 1130a can be moved to the right or the left, for example, when surrounded by engagement members 1106, 1108.

Therefore, as illustrated in FIGS. 21-22a, the positions of the bone fragments in which the reduction fasteners are placed can be fine-tuned, either by being moved apart or by being moved together, or by being tilted and otherwise adjusted with respect to each other.

Examples of the elongate reduction fasteners in the form of pins and screws that are employed to achieve the tilting and fine tuning achieved in the present invention are shown in FIGS. 20A-25. In one embodiment, the elongate reduction fasteners each comprise a non-threaded portion that is at least about as long as the threaded portion of the reduction fasteners, such as shown in FIG. 20A. In one embodiment, the elongate reduction fasteners each comprise a non-threaded portion that is at least as long as the threaded portion of the reduction fasteners.

In another embodiment, the elongate reduction fasteners each comprise a non-threaded portion that is at least about twice as long as the threaded portion of the reduction fasteners. In one embodiment, the elongate reduction fasteners each comprise a non-threaded portion that is at least twice as long as the threaded portion of the reduction fasteners. In yet another embodiment, the elongate reduction fasteners each comprise a non-threaded portion that is at least about three times as long as the threaded portion of the reduction fasteners. In one embodiment, the elongate reduction fasteners each comprise a non-threaded portion that is at least three times as long as the threaded portion of the reduction fasteners. Such elongate reduction fasteners can be used for fine tuning of bone positions and to provide the practitioner significant leverage to effectively manipulate bones.

When elongate reduction fasteners in the form of non-threaded pins, e.g., pins 1130, are employed, in one embodiment, the elongate reduction fastener pins are mounted within bone fragments such that the portions of the pins above respective bone fragments are at least about as long as the portions of the pins mounted within the respective bone fragments. In another embodiment, the elongate reduction fastener pins are mounted within respective bone fragments such that the portions of the pins above the bone fragments are at least as long as the portions of the pins mounted within respective bone fragments.

In another embodiment, the elongate reduction fastener pins are mounted within respective bone fragments such that the portions of the pins above respective bone fragments are at least about twice as long as the portions of the pins mounted within respective bone fragments. In another embodiment, the elongate reduction fastener pins are mounted within respective bone fragments such that the portions of the pins above respective bone fragments are at least twice as long as the portions of the pins mounted within the respective bone fragments. In yet another embodiment, the elongate reduction fastener pins are mounted within respective bone fragments such that the portions of the pins above respective bone fragments are at least about three times as long as the portions of the pins mounted within respective bone fragments. In another embodiment, the elongate reduction fastener pins are mounted within respective bone fragments such that the portions of the pins above the bone fragments are at least three times as long as the portions of the pins mounted within respective bone fragments.

Such elongate reduction fastener pins can be used for fine tuning of bone positions and to provide the practitioner significant leverage to effectively manipulate bones. The longer pins or screws provide more significant leverage and the corresponding ability for fine tuning, tilting, and precise adjustment.

Pins 1130 may be mounted within respective bone portions through contact with a driving tool, for example, or may have a recess in the top portion thereof that enables the use of a rotational screw driving tool or drill, for example. Screws 1130 may have a recess in the top portion thereof configured to enable screws 1130 to be positioned in a desired position in a bone through the use of a rotational screw driving tool or drill, for example.

Figures 23, 24:
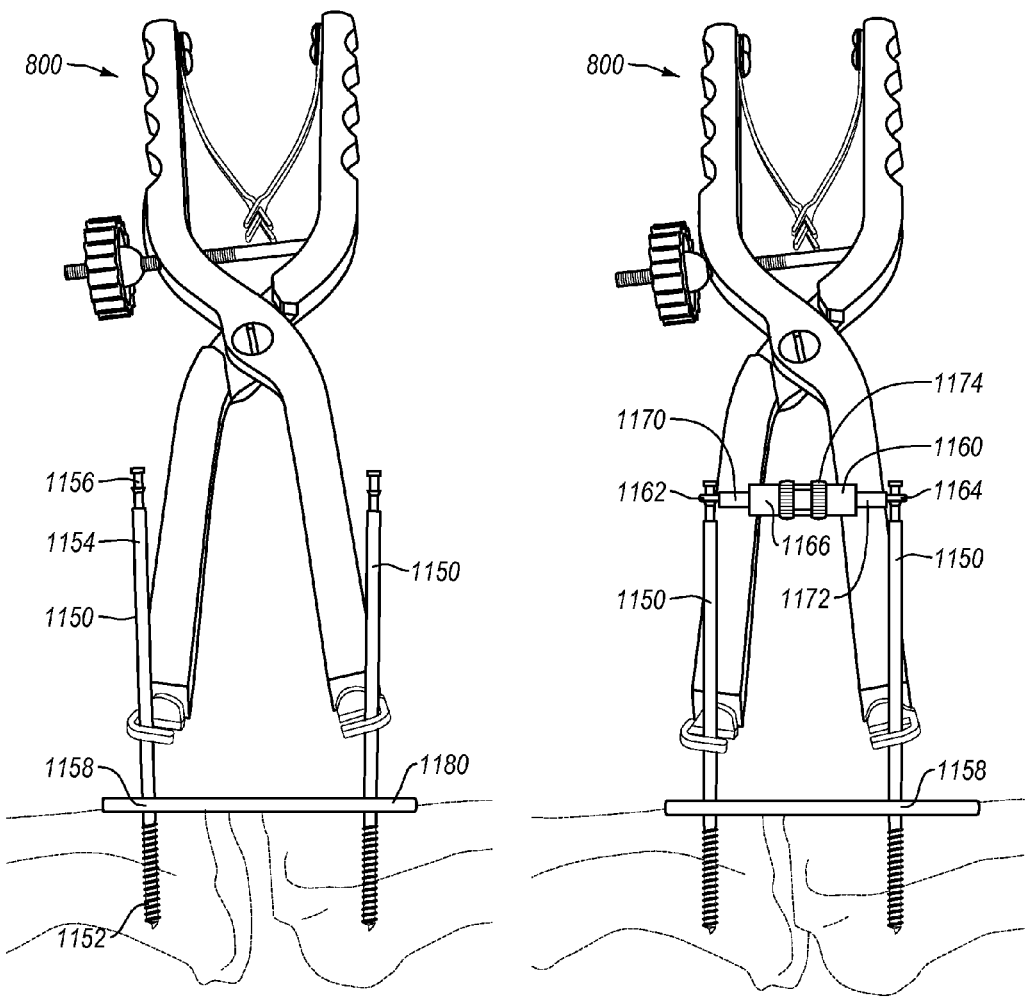
FIG. 23 illustrates the compression clamp of FIGS. 8A-10D mounted on reduction fasteners in the form of elongate screws.
FIG. 24 illustrates a kit of the present invention including: (i) the compression clamp of FIGS. 8A through 10D; (ii) a bone plate; (iii) reduction fasteners in the form of elongate screws extending through the bone plate into opposing bone fragments; and (iv) an adjustable coupler mounted on the upper portions of the elongate screws.

With reference now to FIGS. 23 and 24, in yet another implementation, elongated screws 1150 having threaded lower shaft portions 1152, smooth elongate upper shaft portions 1154, and grooved head portions 1156 (head portions having at least one radial groove therein) mounted on the upper shaft portions 1154 can be employed to extend through a bone plate 1158 for significant leverage and fine tuning with respect to the respective bone discontinuities.

Screws 1150 may have a recess in the top portion thereof configured to enable screws 1150 to be positioned in a desired position in a bone through the use of a rotational screw driving tool or drill, for example. Screws 1150 may optionally have a head portion that is configured, e.g., in a triangle, square or hex pattern so as to receive a rotational tool thereon for insertion within bone fragments, for example.

In order to maintain pins 1150 into a desired location, and/or to more readily manipulate and adjust pins 1150, a coupler 1160, such as or similar to a turnbuckle type coupler, may be mounted on pins 1150, as shown in FIG. 24. When employing coupler 1160, one side of coupler 1160 or both sides may be threadably adjusted, thereby allowing for fine tuning from one side or another, or from both sides using coupler 1160. Coupler 1160 also assists in tilting and other adjustment movements of opposing bone discontinuity portions. Thus, once a clamp, such as clamp 800 has positioned screws 1150 to a certain position with respect to each other, coupler 1160 can be selectively mounted on screws 1150, such that fine tuned adjustments can be performed.

When employing the kit of FIG. 24, clamp 800, or another clamp, such as shown herein, can be employed to initially position screws 1150, after which coupler 1160 can be employed to hold screws 1150 in a desired position and/or to provide additional fine tuning adjustments, such as very slight movement of one screw while maintaining another screw in a fixed position. This is possible because one side of coupler 1160 can be moved while the other remains still. Optionally, both sides of the coupler 1160 can be adjusted.

By tightening one end of coupler 1160 with respect to the other, one pin 1150 can be moved with respect to another pin 1150 in fine turned, precise movements. The use of an adjustable coupler 1160 that enables adjustment of one pin 1150 while the other pin remains still and/or adjustment of both pins 1150 is advantageous because of the fine tuned movements, and adjustments of bone pieces that are enabled.

Coupler 1160 may be in the form of or may be similar to a turnbuckle, stretching screw, or bottlescrew for example. Coupler 1160 has a first eyelet 1162 configured to be mounted on one pin 1150, e.g. to a grooved head portion 1156 of pin 1150, and a second eyelet 1164 configured to be mounted on a grooved head portion 1156 of a second pin 1150, as shown in FIG. 24. In one implementation, for example, coupler 1160 comprises a first threaded member 1170 coupled to eyelet 1162, a second threaded member 1172 coupled to eyelet 1164, and a correspondingly threaded housing 1166 configured to threadedly receive each of the threaded members 1170, 1172. Eyelets 1162, 1164 may be movably, e.g., rotatably, coupled to respective threaded members 1170, 1172 such that members 1170, 1172 can be conveniently, selectively, twisted within housing 1166. The eyelets 1162, 1164 coupled to respective threaded members 1170, 1172 are mounted on the upper portions of the screws 1150, i.e., the portions of the screws extending above the bone plate 1158.

In one implementation, coupler 1160 can be configured to allow adjustment of one end of coupler 1160 at a time, e.g., by turning threaded member 1170 or threaded member 1172 and/or to allow both ends to be adjusted simultaneously by turning housing 1166. In one implementation, one or more threaded grips 1174 can be configured to be used in turning housing 1166. When housing 1166 is turned one way, distraction of the pins 1150 occurs. When housing 1166 is turned another way, compression of the pins 1150 occurs. Thus, the position of one end of coupler 1160 can be adjusted, or of another end can be adjusted, or both ends can be adjusted, thereby selectively providing fine tuning adjustments to the positions of screws 1150 and therefore corresponding bone fragments.

One example of a possible coupler 1160 of the present invention is part of a Fracture Repositioning Instrument (FRI) sold in a Socon Aesculap Spine system, available from Aesculap AG, Am Aesculap-Platz, 78532 Tuttlingen, Germany, although a variety of different useful couplers of the present invention may be employed, for example.

Thus, one embodiment of a kit of the present invention comprises: (i) A compression clamp; e.g. clamp 800, (ii) a pair of reduction fasteners, such as screws 1150; (iii) a coupler 1160 configured to be mounted on the screws 1150 for selectively adjusting the location of the pins with respect to each other; and (iv) a bone plate, e.g., a plate such as plate 1158 or as otherwise described hereinabove. Clamp 800 can be used for compression, while coupler 1160 further provides further fine-tuned adjustments. Coupler 1160 also couples the upper portions of pins 1150 with respect to each other, while plate 1158 orients the bottom portion of pins 1150 with respect to each other.

The kit shown in FIG. 24 enables the practitioner to with both macro adjustments and fined tuned adjustments manipulate bone portions into desired positions with respect to each other, after which the bone portions can be connected permanently together.

The compression plate kit of FIG. 24 enables manual compression control of a bone discontinuity for improved repair of fractures, fusions, and other bone discontinuities. Additionally, the kit of FIG. 24 enables the compression of large gaps between bones, thereby efficient and accurate correction of various different types of bone injury. In light of the use of elongate screws 1150 and/or coupler 1160, the kit of FIG. 24 advantageously provides for fine-tuned adjustments from one side and/or the other of a bone fracture.

Figure 25:
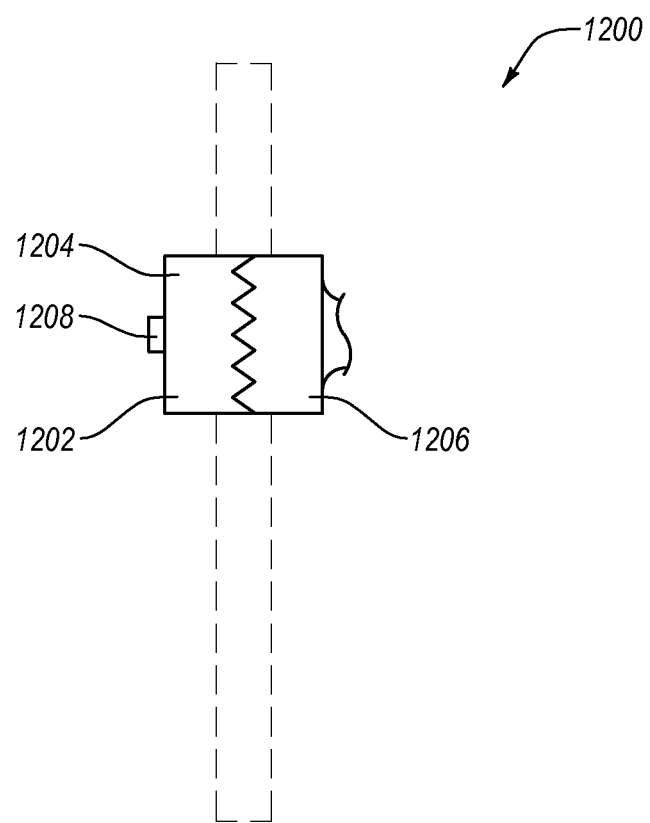
FIG. 25 illustrates a two-part adjustable engagement member of the present invention.

FIG. 25 represents another example of an engagement member 1200 of the present invention that may be pivotally coupled to any of the compression clamp levers disclosed herein, for example. Engagement member 1200 of FIG. 25 has a two-piece mounting chamber 1202, comprising a front portion 1204 and a back portion 1206 that enable member 1200 to be conveniently mounted from the side and/or from above onto a screw, pin, bit, rod, wire, or other reduction fastener.

The engagement member 1200 can also be conveniently adjusted to have a larger inner receiving aperture or a smaller aperture, depending upon the size of the pin or screw used, for example, and depending upon the amount of torque and manipulation force that is desired to be applied. Thus, if a looser torque is desired, the two-piece engaging portion can be adjusted to be looser, for example.

A set screw 1208, or a pair of set screws 1208, for example, can be employed to selectively adjust the size of the engagement member receiving portion. A connector such as a third set screw may be positioned within the mounting chamber and positioned against the reduction fastener to firmly couple the reduction fastener to the engagement member 1200. A screw, a pin, or a smooth rod having the same diameter as a drill bit, for example, or a set or rods, may be employed in connection with engagement member 1200 because it is adjustable to fit various sizes.

In one embodiment, a clamp such as clamp 1100 of FIGS. 19, and 21-22a can be adapted such that engagement members 1106, 1108 are replaced by first and second engagement members 1200 having the configuration shown in FIG. 25. Thus, clamp 1100 can have one or more engagement members 1200 such as illustrated in FIG. 25, for example.

The embodiments of FIGS. 12-25 thus show additional examples of compression plate kits of the present invention that are configured to permit manual reduction of bone discontinuities and of methods for using compression plate kits for repairing bone discontinuities.

Although the kits of the present invention have been described in connection with bone plates, it is also possible to employ the kits of the present invention without the bone plates, such as, for example, during a procedure in which a bone plate is not needed, or is not yet needed as part of the injury repair process. Thus, it is possible to employ the clamps of the present invention without bone plates in connection with the reduction fasteners disclosed, or other reduction fasteners, for example.

One will appreciate in light of the disclosure herein that the present invention may be embodied in other specific forms without departing from its spirit or essential characteristics. In addition, the structures and processes described herein can be deviated in any number of ways within the context of implementations of the present invention. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

I claim:
1. A surgical kit for use in surgically repairing bone having first and second bone portions, the kit comprising:
   a bone plate having one or more fixation holes and at least one slide channel, the bone plate configured to be placed across a bone discontinuity, wherein the bone discontinuity comprises one of a bone joint or a bone fracture;
   first and second reduction fasteners, wherein the first reduction fastener is adapted to be positioned within a first fixation hole of said bone plate, and wherein the second fastener is adapted to be positioned within said at least one slide channel and secured to a second bone portion; and
a compression clamp having a pair of engagement members adapted to engage said first and second reduction fasteners, said clamp adapted to draw said second reduction fastener along said at least one slide channel toward said first fastener,
wherein the first engagement member is configured to be positioned about an exterior surface of the first reduction fastener and wherein the second engagement member is configured to be positioned about an exterior surface of the second reduction fastener, and wherein the compression clamp is configured to be closed by manually squeezing together handles of the compression clamp, thereby drawing the second reduction fastener and the second bone portion along the slide channel toward the first reduction fastener and the first bone portion, and further comprising:
a first fixation fastener and a second fixation fastener, such that the first fixation fastener is configured to be secured to the bone plate and to the first bone portion, such that the second fixation fastener is configured to be secured to the bone plate and to the second bone portion; and
a coupler configured to couple upper portions of the reduction fasteners to each other and to enable selective adjustment of the positions of the reduction fasteners, wherein the coupler is coupled to the first and second reduction fasteners proximally of the compression clamp.

2. The kit of claim 1, wherein said engagement members comprise mounting chambers having respective apertures therein, the engagement members configured to slidably receive respective fasteners within the engagement members.

3. The kit of claim 1, wherein the engagement members comprise ost-shaped mounting portions.

4. The kit of claim 3, wherein the reduction fasteners each have a head mounted on a shaft, the head having an aperture therethrough.

5. The kit of claim 1, wherein the reduction fasteners each have a head mounted on a shaft, the head have a U-shape.

6. The kit of claim 1, wherein at least one of the engagement members comprises a two-part adjustable engagement member.

7. The kit of claim 6, wherein the two-part engagement member can be adjusted so as to adjust the size of an aperture extending through the engagement member.

8. The kit of claim 1, wherein the engagement members have a U-shaped mounting portion.

9. The kit of claim 1, wherein the reduction fasteners comprise first and second elongate screws, each of the elongate screws comprising a non-threaded portion that is at least about as long as a threaded portion of the screws.

10. The kit of claim 9, wherein the reduction fasteners comprise first and second elongate screws, each of the elongate screws comprising a non-threaded portion that is at least about three times as long as a threaded portion of the screws.

11. The kit of claim 1, wherein each of the engagement members comprises a mounting chamber, the mounting chamber having an aperture therethrough for receiving a fastener therein and further comprises a connector for coupling the fastener to the mounting chamber.

12. The kit of claim 1, wherein the first engagement feature of the first reduction fastener comprises a neck of reduced diameter.

13. A kit for use in correcting bone, comprising:
a bone plate adapted to be used in a procedure to secure a first bone portion to a second bone portion, said bone plate comprising a first fixation hole, an slide channel, and a second fixation hole;
a first reduction fastener, said first reduction fastener being adapted to be inserted within said second fixation hole and secured to the first bone portion;
a second reduction fastener, said second reduction fastener being adapted to be inserted within said slide channel and secured to the second bone portion;
a compression clamp, said compression clamp comprising a first engagement member and a second engagement member, said first engagement member being sized and configured to be mounted on an exterior surface of said first fixation reduction fastener, said second engagement member being sized and configured to be mounted on an exterior surface of said second reduction fastener, said compression clamp being configured to draw said second reduction fastener along said slide channel toward said first reduction fastener, thereby pulling the second bone portion toward the first bone portion; and
a coupler configured to couple the upper portions of the reduction fasteners to each other and to enable selective adjustment of the positions of the reduction fasteners, wherein the coupler is coupled to the first and second reduction fasteners proximally of the compression clamp.

14. The kit of claim 13, wherein said coupler is selectively mounted on the reduction fasteners and is selectively adjustable from one side or another.

15. The kit of claim 13, wherein the first engagement member is configured to be positioned about an exterior surface of the first reduction fastener and wherein the second engagement member is configured to be positioned about an exterior surface of the second reduction fastener and wherein the compression clamp is configured to be closed by manually squeezing together handles of the compression clamp, thereby drawing the second reduction fastener and the second bone portion along the slide channel toward the first reduction fastener and the first bone portion, and further comprising:
a first fixation fastener and a second fixation fastener, such that the first fixation fastener is configured to be secured to the bone plate and to the first bone portion, and such that the second fixation fastener is configured to be secured to the bone plate and to the second bone portion.

* * * * *